United States Patent
Hong et al.

(10) Patent No.: US 10,933,409 B2
(45) Date of Patent: Mar. 2, 2021

(54) TRANSITION METAL COMPLEX CONTAINING SULFONAMIDE OR AMIDE GROUP FOR OLEFIN METATHESIS REACTION AND APPLICATION THEREOF

(71) Applicant: Seoul National University R&DB Foundation, Seoul (KR)

(72) Inventors: Soon Hyeok Hong, Seoul (KR); Gunsoon Kim, Seoul (KR); Gitaek Song, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 197 days.

(21) Appl. No.: 16/072,192

(22) PCT Filed: Jan. 25, 2017

(86) PCT No.: PCT/KR2017/000913
§ 371 (c)(1),
(2) Date: Jul. 24, 2018

(87) PCT Pub. No.: WO2017/135638
PCT Pub. Date: Aug. 10, 2017

(65) Prior Publication Data
US 2019/0030521 A1  Jan. 31, 2019

(30) Foreign Application Priority Data
Feb. 1, 2016  (KR) .................. 10-2016-0012349

(51) Int. Cl.
*B01J 31/22* (2006.01)
*C07F 15/00* (2006.01)
*B01J 31/16* (2006.01)
*C07F 15/06* (2006.01)
*C07F 15/02* (2006.01)
*C07C 67/333* (2006.01)
*C07C 201/00* (2006.01)
*C07C 29/00* (2006.01)
*C07C 67/30* (2006.01)
*C07D 207/20* (2006.01)
*C07D 207/48* (2006.01)
*C07D 211/96* (2006.01)

(52) U.S. Cl.
CPC .......... *B01J 31/2278* (2013.01); *B01J 31/16* (2013.01); *B01J 31/2226* (2013.01); *C07C 29/00* (2013.01); *C07C 67/30* (2013.01); *C07C 67/333* (2013.01); *C07C 201/00* (2013.01); *C07D 207/20* (2013.01); *C07D 207/48* (2013.01); *C07D 211/96* (2013.01); *C07F 15/00* (2013.01); *C07F 15/0046* (2013.01); *C07F 15/02* (2013.01); *C07F 15/06* (2013.01); *B01J 2231/543* (2013.01); *B01J 2531/821* (2013.01); *C07C 2601/10* (2017.05)

(58) Field of Classification Search
None
See application file for complete search history.

(56) References Cited

U.S. PATENT DOCUMENTS

2007/0043180 A1  2/2007  Zhan

FOREIGN PATENT DOCUMENTS

JP         5365625 B2      12/2013
KR   1020140131553 A      11/2014

OTHER PUBLICATIONS

Venkata R. Sabbasani et al.; Structure and reactivity of sulfonamide- and acetate-chelated ruthenium alkylidene complexes; Organic Chemistry Frontiers; May 23, 2016, vol. 3; No. 8; pp. 939-943; Royal Society of Chemistry; Cambridge, UK.
J. N. Coalter III et al.; Coordinated carbenes from electron-rich olefins on RuHCl(PPr3i)2; New Journal of Chemistry; 2000; vol. 24; No. 1; pp. 9-26; Royal Society of Chemistry; Cambridge, UK.
L. Schiaffino et al.; Rhodium-catalysed hydrogenation of enamides with monodentate phosphorous ligands. A density functional theory study; Journal of Physical Organic Chemistry; 2011; vol. 24; No. 3; pp. 257-261; John Wiley & Sons; Hoboken, NJ, USA.
International Search Report of PCT/KR2017/000913, dated May 11, 2017, English Translation.
Anna Szadkowska et al.; Ruthenium Olefin Metathesis Catalysts Containing Six-Membered Sulfone and Sulfonamide Chelating Rings; Organometallics; 2011; 30, pp. 1130-1138; American Chemical Society; USA.

*Primary Examiner* — Yun Qian
(74) *Attorney, Agent, or Firm* — STIP Law Group, LLC

(57) ABSTRACT

Disclosed is a novel transition metal complex containing N-heterocyclic carbene and a sulfonamide group, or N-heterocyclic carbene and an amide group, and application thereof, the traquesnsition metal complex having a wider range of general purposes in olefin metathesis and being able to be variably controlled in reactivity.

10 Claims, 3 Drawing Sheets

TRANSITION METAL COMPLEX CONTAINING SULFONAMIDE OR AMIDE GROUP FOR OLEFIN METATHESIS REACTION AND APPLICATION THEREOF

CROSS-REFERENCE TO RELATED APPLICATIONS

This application is the U.S. National Phase under 35 U.S.C. § 371 of International Application No. PCT/KR2017/000913 filed on Jan. 25, 2017, which in turn claims the benefit of Korean Applications No. 10-2016-0012349, filed on Feb. 1, 2016, and No. 10-2016-0137291, filed on Oct. 21, 2016, the disclosures of which are incorporated by reference into the present application.

TECHNICAL FIELD

The present disclosure relates to a transition metal complex containing a sulfonamide or amide group for olefin metathesis and application thereof and, more particularly, to a novel transition metal complex containing N-heterocyclic carbene and a sulfonamide group, or N-heterocyclic carbene and an amide group, which has a wider range of general purposes in olefin metathesis and can be variably controlled in reactivity, and an olefin metathesis reaction using the same.

BACKGROUND ART

Olefin metathesis has become a valuable synthesis method for construction of a carbon-carbon double bond, particularly finding applications in organic synthesis and polymer synthesis.

Studies on catalysts for olefin metathesis reactions proposed the use of homogeneous catalysts using transition metal complexes. Ongoing studies have been conducted on methods in which transition metal complexes, inter alia, transition metal carbene compounds are prepared and used as olefin metathesis catalysts.

Of conventional techniques relevant to olefin metathesis, U.S. Patent No. 2007/0043180 A (Feb. 22, 2007) introduces an olefin metathesis reaction using a transition metal complex which contains a carbene ligand with an ether functional group coordinated to the central metal ruthenium and Korean Patent No. 10-2014-0131553 (Nov. 13, 2014) discloses an olefin metathesis reaction using a complex which contains a quaternary onium group in an inert ligand.

However, conventional transition metal complexes containing carbene ligands suffer from the disadvantage of designing and obtaining carbene ligands through complicated multi-stage reactions and requiring a stoichiometric amount of a Wittig reagent, which is difficult to handle. In addition, conventional transition metal complexes are, for the most part, limited with respect to the suitable substitution or change of ligands for carbene to introduce various substituents.

Therefore, there is still the continuous need for studies on the development of novel transition metal catalysts that can be appropriately controlled by introducing suitable ligands into transition metal complexes to meet the catalytic efficiency and reactivity desired by users.

DETAILED DESCRIPTION OF THE INVENTION

Technical Problem

In order to solve the above problems, the present disclosure provides a novel transition metal complex containing a phosphine or N-heterocyclic carbene ligand and a sulfonamide or amide group, and a preparation method thereof.

In addition, the present disclosure provides a method for conducting an olefin metathesis reaction by using the transition metal complex as a catalyst.

Further, the present disclosure provides a novel catalyst for olefin metathesis reactions, the catalyst containing a phosphine or N-heterocyclic carbene ligand, and a sulfonamide or amide group.

Technical Solution

The present disclosure provides a transition metal complex represented by the following Chemical Formula A:

    [Chemical Formula A]

wherein,

M is a transition metal,

L1 means a phosphine ligand or N-heterocyclic carbene ligand containing a substituted or unsubstituted alkyl of 1 to 30 carbon atoms or a substituted or unsubstituted aryl of 6 to 30 carbon atoms, L2 and L3, which may be the same or different, are each a monovalent ligand selected from among a hydrogen atom, a deuterium atom, a halogen, a cyano, a substituted or unsubstituted alkyl of 1 to 30 carbon atoms, a substituted or unsubstituted aryl of 6 to 50 carbon atoms, a substituted or unsubstituted arylalkyl of 7 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted arylthioxy of 6 to 30 carbon atoms, a substituted or unsubstituted alkylthioxy of 1 to 30 carbon atoms, a substituted or unsubstituted heteroaryl of 2 to 50 carbon atoms bearing O, N, or S as a heteroatom, a substituted or unsubstituted carboxylate anion of 1 to 30 carbon atoms, and a nitrate (NO3-); or, a neutral ligand selected from among a phosphine containing a substituted or unsubstituted alkyl of 1 to 30 carbon atoms or a substituted or unsubstituted aryl of 6 to 50 carbon atoms, carbon monoxide, an amine containing a substituted or unsubstituted alkyl of 1 to 30 carbon atoms or a substituted or unsubstituted aryl of 6 to 50 carbon atoms, a nitrile containing a substituted or unsubstituted alkyl of 1 to 30 carbon atoms or a substituted or unsubstituted aryl of 6 to 50 carbon atoms, and a substituted or unsubstituted aromatic heterocyclic compound of 2 to 50 carbon atoms bearing O, N, or S as a heteroatom;

in the alterative for L2 and L3, L2 and L3 may be connected to each other to form a ring with M and when L2 and L3 are each plural, the corresponding plural L2's or L3's are connected to each other to form a ring with M, n and m, which may be the same or different, are each independently an integer of 0 to 2 and when n or m is 2 or greater, the corresponding plural L2's or L3's may be the same or different, and A is a ligand containing a sulfonamide group or an amide group.

In addition, the present disclosure provides a method for preparing a transition metal complex represented by Chemical Formula A, the method comprising contacting a transition metal complex as a reactant with a double bond-containing sulfonamide or a double bond-containing amide wherein the reactant transition metal complex contains an N-heterocyclic carbene ligand; or a phosphine ligand containing a substituted or unsubstituted alkyl of 1 to 30 carbon atoms or a substituted or unsubstituted aryl of 6 to 30 carbon atoms; plus an additional carbene ligand; and does neither contain sulfonamide nor amide as a ligand, and the double bond-containing sulfonamide or double bond-containing amide is substituted for the additional carbene in the transition metal complex to afford the transition metal complex represented by Chemical Formula A.

In addition, the present disclosure provides a method for conducting an olefin metathesis reaction by using the transition metal complex as a catalyst.

Further, the present disclosure provides a catalyst for olefin metathesis, which is obtained by supporting the transition metal complex on a carrier.

Further, the present disclosure provides a catalyst for olefin metathesis, the catalyst being represented by the following Chemical Formula D:

$$(L1)M(B)(L2)n(L3)m \quad \text{[Chemical Formula D]}$$

wherein,

M is a transition metal,

L1 means a phosphine ligand or N-heterocyclic carbene ligand containing a substituted or unsubstituted alkyl of 1 to 30 carbon atoms or a substituted or unsubstituted aryl of 6 to 30 carbon atoms, L2 and L3, which may be the same or different, are each independently a monovalent ligand selected from among a hydrogen atom, a deuterium atom, a halogen, a cyano, a substituted or unsubstituted alkyl of 1 to 30 carbon atoms, a substituted or unsubstituted aryl of 6 to 50 carbon atoms, a substituted or unsubstituted arylalkyl of 7 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted arylthioxy of 6 to 30 carbon atoms, a substituted or unsubstituted alkylthioxy of 1 to 30 carbon atoms, a substituted or unsubstituted heteroaryl of 2 to 50 carbon atoms bearing O, N, or S as a heteroatom, a substituted or unsubstituted carboxylate anion of 1 to 30 carbon atoms, and a nitrate ($NO^{3-}$); or a neutral ligand selected from among a phosphine containing a substituted or unsubstituted alkyl of 1 to 30 carbon atoms or a substituted or unsubstituted aryl of 6 to 5 carbon atom, an amine containing a carbon monoxide, a substituted or unsubstituted 3 alkyl of 1 to 30 carbon atoms or a substituted or unsubstituted aryl of 6 to 50 carbon atoms, a nitrile containing a substituted or unsubstituted alkyl of 1 to 30 carbon atoms or a substituted or unsubstituted aryl of 6 to 50 carbon atoms, and a substituted or unsubstituted aromatic heterocyclic compound of 2 to 50 carbon atoms bearing O, N, or S as a heteroatom;

in the alterative for L2 and L3, L2 and L3 may be connected to each other to form a ring with M and when L2 and L3 are each plural, the plural L2's or L3's may be connected to each other to form a ring with M, n and m, which may be the same or different, are each independently an integer of 0 to 2 and when n or m is 2, the corresponding L2's or L3's may be the same or different, and B is represented by A'-P, wherein A' is a radical resulting from removal of one of hydrogens bound to carbon atoms in a sulfonamide or amide group, P is a carrier radical resulting from removal of one hydrogen from an intact carrier thereof, and A' and P form a covalent bond via which the carrier is connected to the sulfonamide or amide.

Advantageous Effect

It is difficult to properly introduce desired substituents to homogeneous catalysts, reported up to now, for use in double-bond metathesis not only because multi-stage synthesis is needed for the synthesis of a carbene ligand, but also because limitations are imparted to the introduction of various substituents to ligands. However, the novel compound represented by Chemical Formula A in accordance with the present disclosure allows various substituents to be easily introduced to the sulfonamide or amide moiety thereof, thereby enjoying the advantage of being variably controlled in catalytic activity or reactivity for metathesis.

In addition, a double bond-containing sulfonamide or amide ligand for the introduction of a carbene ligand to construct a transition metal complex can be prepared only in two steps according to the present disclosure. Further, the structural versatility of the sulfonamide or amide itself allows the synthesis of ligands showing various structural and electrical properties and is thus economically advantageous to the supply of ligands. Moreover, the present disclosure can make easier access to the reactions necessary for the preparation of the double bond-containing sulfonamide or amide and is more environmentally friendly due to the absence of phosphine oxide as a by-product by use of vinyl acetate, compared to the Wittig reagents for use in preparing conventional double bond-containing ligands.

The transition metal complex of the present disclosure has an outstanding activity as a catalyst for olefin metathesis and can be advantageously controlled in activity by introducing suitable substituents into the ligands thereof.

BEST MODE FOR INVENTION

Figure 1:
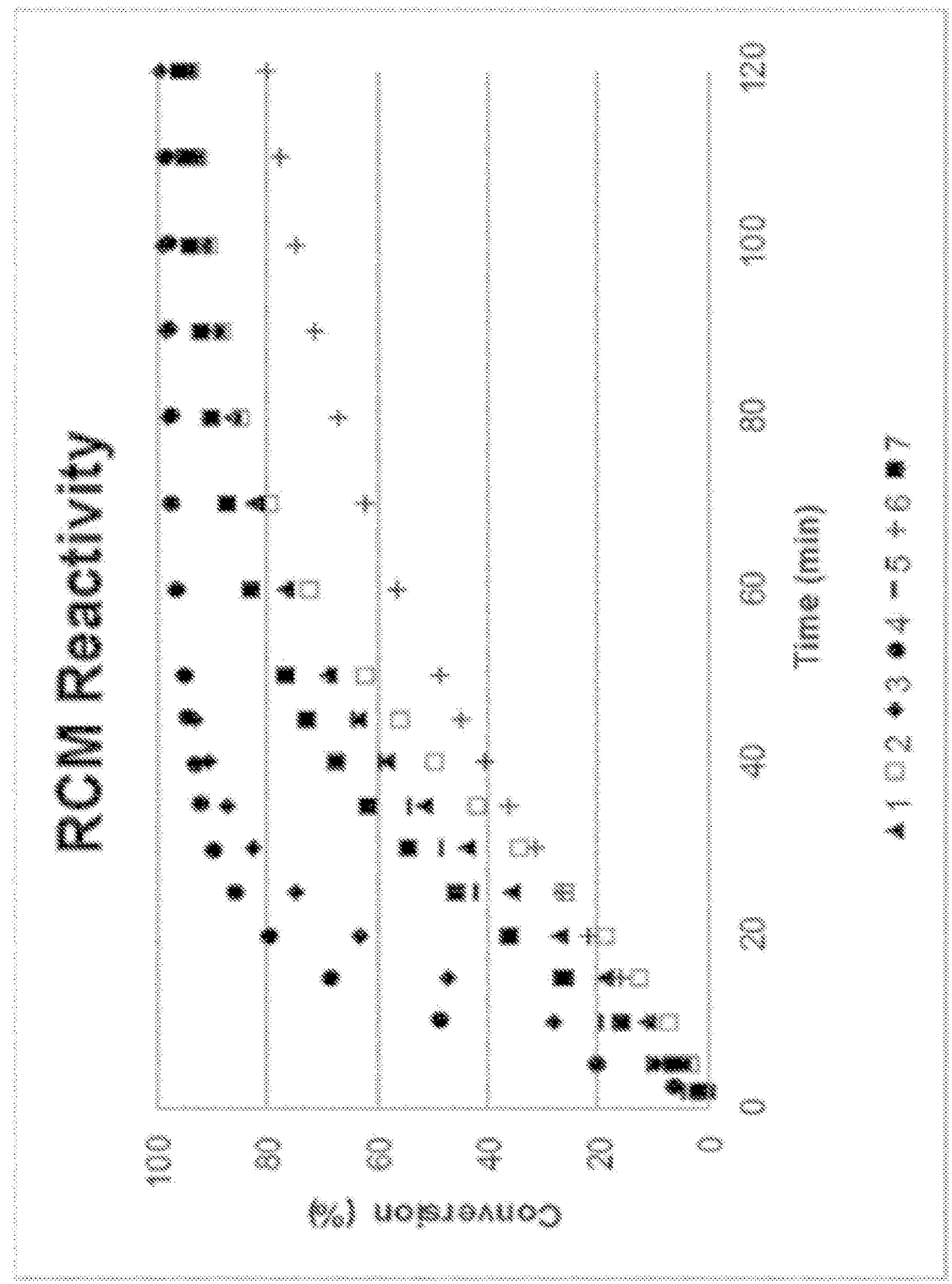
FIG. 1 depicts the activity of a catalyst containing a sulfonamide ligand prepared according to an embodiment of the present disclosure (Examples 1 to 7).

Specific features and advantages of the present invention will be more clearly understood from the following detailed description when taken in conjunction with the accompanying drawings. In the following description, it is to be noted that, when the functions of conventional elements and the detailed description of elements related with the present invention may make the gist of the present invention unclear, a detailed description thereof will be omitted.

The present disclosure pertains to a transition metal complex containing an N-heterocyclic carbene ligand in addition to a sulfonamide or amide as a ligand.

In greater detail, the transition metal complex according to the present disclosure is represented by the following Chemical Formula A:

(L1)M(A)(L2)n(L3)m     [Chemical Formula A]

wherein,

M is a transition metal,

L1 means a phosphine ligand or N-heterocyclic carbene ligand containing a substituted or unsubstituted alkyl of 1 to 30 carbon atoms or a substituted or unsubstituted aryl of 6 to 30 carbon atoms, L2 and L3, which may be the same or different, are each a monovalent ligand selected from among a hydrogen atom, a deuterium atom, a halogen, a cyano, a substituted or unsubstituted alkyl of 1 to 30 carbon atoms, a substituted or unsubstituted aryl of 6 to 50 carbon atoms, a substituted or unsubstituted arylalkyl of 7 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted arylthioxy of to 30 carbon atoms, a substituted or unsubstituted alkyl-thioxy of 1 to 30 carbon atoms, a substituted or unsubstituted heteroaryl of 2 to 50 carbon atoms bearing O, N, or S as a heteroatom, a substituted or unsubstituted carboxylate anion of 1 to 30 carbon atoms, and a nitrate (NO3-); or, a neutral ligand selected from among a phosphine containing a substituted or unsubstituted alkyl of 1 to 30 carbon atoms or a substituted or unsubstituted aryl of 6 to 50 carbon atoms, carbon monoxide, an amine containing a substituted or unsubstituted alkyl of 1 to 30 carbon atoms or a substituted or unsubstituted aryl of 6 to 50 carbon atoms, a nitrile containing a substituted or unsubstituted alkyl of 1 to 30 carbon atoms or a substituted or unsubstituted aryl of 6 to 50 carbon atoms, and a substituted or unsubstituted aromatic heterocyclic compound of 2 to 50 carbon atoms bearing O, N, or S as a heteroatom;

in the alterative for L2 and L3, L2 and L3 may be connected to each other to form a ring with M, and when L2 and L3 are each plural, the corresponding plural L2's or L3's are connected to each other to form a ring with M, n and m, which may be the same or different, are each independently an integer of 0 to 2 and when n or m is 2 or greater, the corresponding plural L2's or L3's may be the same or different, and A is a ligand containing a sulfonamide group or an amide group.

As used herein, the term 'substituted' in the expression 'substituted or unsubstituted' means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

The expression indicating the number of carbon atoms, such as "a substituted or unsubstituted alkyl of 1 to 30 carbon atoms", "a substituted or unsubstituted aryl of 6 to 50 carbon atoms", etc. means the total number of carbon atoms of, for example, the alkyl or aryl radical or moiety alone, exclusive of the number of carbon atoms of substituents attached thereto. For instance, a phenyl group with a butyl at the para position falls within the scope of an aryl of 6 carbon atoms, even though it is substituted with a butyl radical of 4 carbon atoms.

As used herein, the term "aryl" means an organic radical derived from an aromatic hydrocarbon by removing one hydrogen that is bonded to the aromatic hydrocarbon. It may be a single or fused aromatic system. Further, the aromatic system may include a fused ring that is formed by adjacent substituents on the aryl radical.

Examples of the aryl include aromatic groups, such as phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl. At least one hydrogen atom of the aryl may be substituted by a deuterium atom, a halogen atom, a hydroxy, a nitro, a cyano, a silyl, an amino (—$NH_2$, —NH(R), —N(R') (R") wherein R' and R" are each independently an alkyl of 1 to 10 carbon atoms, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms, or a heteroarylalkyl of 2 to 24 carbon atoms.

As used herein, the term "heteroaryl", which is used as a substituent in the compound of the present disclosure, refers to a cyclic aromatic system of 2 to 24 carbon atoms bearing 1, 2, or 3 heteroatoms selected from among N, O, P, Si, S, Ge, Se, and Te as a ring member(s). At least one hydrogen atom on the heteroaryl may be substituted by the same substituent as in the aryl.

In addition, the term "heteroaromatic ring", as used herein, refers to an aromatic ring bearing as a ring member at least one heteroatom selected from among N, O, P, Si, S, Ge, Se, and Te.

Examples of the alkyl substituent useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Examples of the alkoxy substituent useful in the present disclosure include methoxy, ethoxy, propoxy, isobutyloxy, sec-butyloxy, pentyloxy, iso-amyloxy, and hexyloxy. At least one hydrogen atom of the alkoxy may be substituted by the same substituent as in the aryl.

Meanwhile, 'A' in the catalyst according to the present disclosure may be a ligand represented by the following Structural Formula A-1 or A-2:

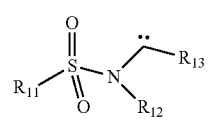     [Structual A-1]

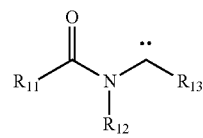     [Structual A-2]

wherein,

R11 to R13, which may be the same or different, are each independently selected from among a hydrogen atom, a deuterium atom, a substituted or unsubstituted alkyl of 1 to 30 carbon atoms, a substituted or unsubstituted 7 aryl of 6 to 50 carbon atoms, a substituted or unsubstituted cycloalkyl of 3 to 30 carbon atoms, a substituted or unsubstituted heteroaryl of 2 to 50 carbon atoms bearing at least one selected from among O, N, S, and Si as a heteroatom, a substituted or unsubstituted alkoxy of 1 to 30 carbon atoms, a substituted or unsubstituted aryloxy of 6 to 30 carbon atoms, a substituted or unsubstituted alkylamine of 1 to 30 carbon atoms, a substituted or unsubstituted aryl amine of 6 to 30 carbon atoms, a substituted or unsubstituted alkylsilyl of 1 to 30 carbon atoms, a substituted or unsubstituted arylsilyl of 6 to 30 carbon atoms, a cyano, and a halogen, and '...' means a pair of electrons of carbene.

Here, 'substituted' in the expression "substituted or unsubstituted" given to the substituents R11 to R13 has the same meaning as that for the ligands L2 and 3.

By way of example, at least one of the substituents R11 to R13 may contain one or more fluorine atoms which may be positioned, instead of a part or all of hydrogens, on an alkyl, an aryl, a cycloalkyl, a heteroaryl, an alkoxy, an aryloxy, an alkylamine, an arylamine, etc.

In addition, the sulfonamide containing a preferable vinyl group may be, for example, one selected from the ligands represented by the following formulas 1L to 10L.

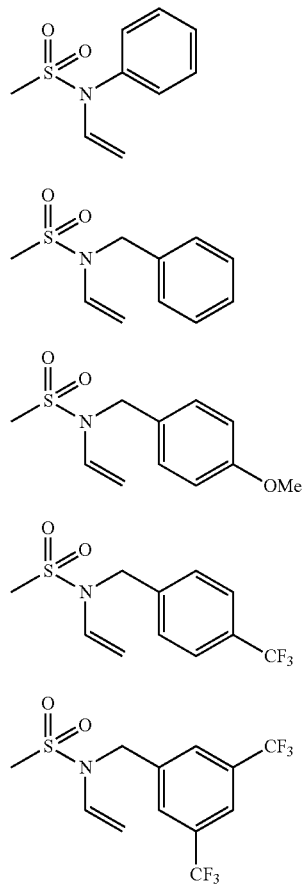

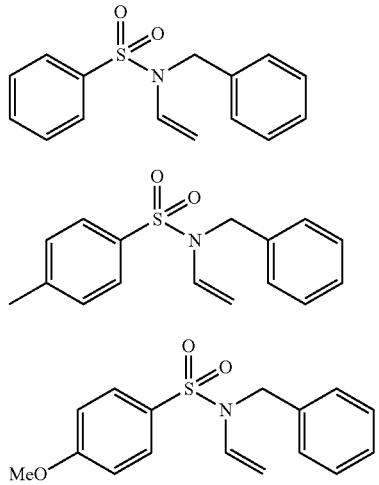

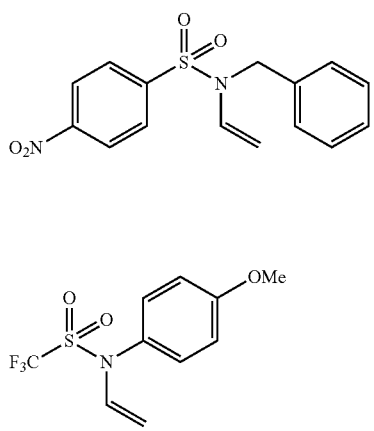

In the case where the sulfonamide is used as a ligand coordinating to a transition metal in accordance with the present disclosure, an oxygen atom of the sulfonyl moiety and a carbon atom of the carbene moiety in the sulfonamide represented by Structural Formula A-1 may be bound to the transition metal such as ruthenium, as shown in the following Structural Formula 1:

[Structural Formula 1]

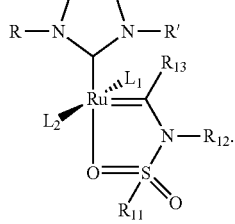

When an amide serves as a ligand coordinating to a transition metal, an oxygen atom and a carbon atom of the carbene moiety in the amide represented by Structural Formula A-2 may be bound to the transition metal such as ruthenium, as shown in the following Structural Formula 2:

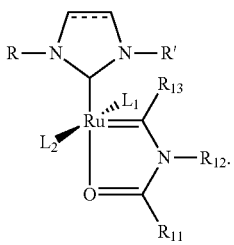

[Structural Formula 2]

In Structural Formulas 1 and 2, the ruthenium atom-bound, 5-membered ring ligand bearing two nitrogen atoms is an exemplary structure of the N-heterocyclic carbene ligand, L1 and L2 mean respective monovalent ligands, the substituents R11 to R13 in the sulfonamide and the amide are as defined above, the substituents R and R1 in the N-heterocyclic carbene ligand may be as defined for the substituents R11 to R13 in the sulfonamide and the amide.

In addition, the reaction behavior of olefin metathesis which the complex in the present disclosure participates can be controlled by properly selecting the substituents R11 to R13 in the sulfonamide or amide.

In greater detail, when an electron donating group is given for the substituents, the catalyst shows slow activity. On the other hand, an electron withdrawing group, when given for the substituents, can elicit fast catalytic activity.

For example, the use of a fluorine atom-bearing substituent as at least one of the substituents R11 to R13 introduces an electron withdrawing characteristic into the substituents, thereby eliciting fast catalytic activity in olefin metathesis reactions.

In addition, the N-heterocyclic carbene ligand according to the present disclosure may be represented by the following Chemical Formula B:

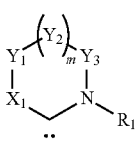

[Chemical Formula B]

wherein

X1 is selected from among O, S, N—R2, C—R3, and C—R4R5, a single or a double bond may be between X1 and Y1, between Y1 and Y2, and between Y2 and Y3, Y1 to Y3, which may be the same or different, are each independently selected from among N, N—R6, C—R7, and C—R8R9, m is an integer of 0 to 3 and when m is 2 or greater, the corresponding plural Y2's may be the same or different, with a single or a double bond therebetween, R1 to R9, which may be the same or different, are each independently selected from among a hydrogen atom, a deuterium atom, a halogen, a substituted or unsubstituted alkyl of 1 to 30 carbon atoms, a substituted or unsubstituted aryl of 6 to 50 carbon atoms, a substituted or unsubstituted arylalkyl of 7 to 50 carbon atoms, a substituted or unsubstituted cycloalkyl of 3 to 30 carbon atoms, a substituted or unsubstituted alkoxy of 1 to 30 carbon atoms, a substituted or unsubstituted aryloxy of 6 to 30 carbon atoms, and a substituted or unsubstituted heteroaryl of 2 to 50 carbon atoms bearing O, N, or S as a heteroatom, with a proviso that R1 and R2 are each neither a hydrogen atom nor a deuterium atom, and ' . . . ' means a pair of electrons in carbene.

In the present disclosure, the N-heterocyclic carbene can be obtained by deprotonating an N-heterocyclic carbene precursor salt with a base. In this regard, so long as it is converted into N-heterocyclic carbene, which is a heterocyclic carbene derivative bearing a nitrogen atom, via deprotonation, any N-heterocyclic carbene precursor salt may be employed irrespective of kinds thereof. For example, the N-heterocyclic carbene precursor salt may be a compound represented by the following Chemical Formula C:

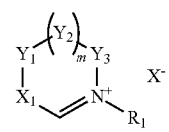

[Chemical Formula C]

wherein

X1 is selected from among O, S, N—R2, C—R3, and C—R4R5, a single or a double bond may be between X1 and Y1, between Y1 and Y2, and between Y2 and Y3, Y1 to Y3, which may be the same or different, are each independently selected from among N, N—R6, C—R7, and C—R8R9, m is an integer of 0 to 3, and when m is 2 or greater, the corresponding Y2's may be the same or different, with a single or a double bond therebetween, R1 to R9 are each independently selected from among a hydrogen atom, a deuterium atom, a halogen, alkyl of 1 to 30 carbon atoms, an aryl of 5 to 50 carbon atoms, an arylalkyl of 5 to 50 carbon atoms, an alkenyl of 2 to 30 carbon atoms, a substituted or unsubstituted alkynyl of 2 to 20 carbon atoms, a cycloalkyl of 3 to 30 carbon atoms, a cycloalkenyl of 5 to 30 carbon atoms, an alkoxy of 1 to 30 carbon atoms, an aryloxy of 6 to 30 carbon atoms, a heteroaryl of 2 to 50 carbon atoms bearing O, N, or S as a heteroatom, with a proviso that R1 and R2 are neither a hydrogen atom nor a deuterium atom, X— is a monovalent anion for charge balance with a cation of the N-heterocyclic carbene precursor.

By way of example, X— may be a monovalent anion such as a halogen anion, a sulfonate anion (RSO3-, wherein R is alkyl, aryl, cycloalkyl, etc.), a tetrafluoroborate anion (BF4-), a hexafluorophosphate anion (PF6-), a triflate anion (—OTf), etc.

In Chemical Formula B, when X1 is a carbon atom having R3 bonded thereto, R3 may be a substituent which is neither a hydrogen atom nor a deuterium atom, and at least one of R4 and R5 is preferably a substituent other than a hydrogen atom or a deuterium atom.

The N-heterocyclic carbene precursor represented by Chemical Formula C may be converted into N-heterocyclic carbene by deprotonation with a base.

In this regard, the deprotonation of the N-heterocyclic carbene precursor with a base can be represented by the following Reaction Scheme A:

[Reaction Scheme A]

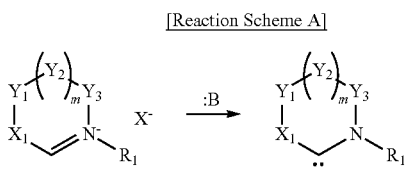

wherein R1, X1, Y1 to Y3, m, and X are respectively as defined above, and B is a base to deprotonate the carbon between X1 and the nitrogen atom to afford N-heterocyclic carbene.

So long as it has basicity sufficient to deprotonate the carbon between X1 and the nitrogen atom in the N—N-heterocyclic carbene precursor, any base may be used for deprotonation of the N-heterocyclic carbene precursor into N-heterocyclic carbene irrespective of kinds thereof. In some particular embodiments, the base may be selected from among alkali metal hydride; alkali metal hydroxide; alkali metal alkoxide; an alkali metal salt of primary or secondary deprotonated amine; and an alkali metal salt of an alkyl anion of 1 to 30 carbon atoms, an alkyl anion of 1 to 30 carbon atoms, a cycloalkyl anion of 3 to 40 carbon atoms, or an aryl anion of 6 to 30 carbon atoms.

For example, the base may be NaH, KH, LiH, etc. as alkali metal hydrides, KOH, NaOH, etc. as alkali metal hydroxides, KOtBu as alkali metal alkoxide, KOtBu as alkali metal alkoxide, NaNH2, LDA (Lithium diisopropyl-amide), etc. as alkali metal salts of deprotonated ammonia or primary or secondary amine, and MeLi, n-BuLi, t-BuLi, PhLi, etc. as alkali metal salts of an alkyl anion of 1 to 30 carbon atoms, an alkyl anion of 1 to 30 carbon atoms, a cycloalkyl anion of 3 to 40 carbon atoms, or an aryl anion of 6 to 30 carbon atoms.

Further, a base for deprotonating an N-heterocyclic carbene precursor may be used at a molar ratio 1 to 10 equivalents to the N-heterocyclic carbene precursor.

In greater detail, the N-heterocyclic carbene ligand in the complex represented by Chemical Formula A in accordance with the present disclosure may be represented by one selected from among Chemical Formulas B-1 to B-13:

[Chemical Formula B-1]

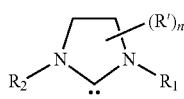

[Chemical Formula B-2]

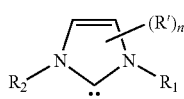

[Chemical Formula B-3]

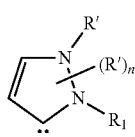

[Chemical Formula B-4]

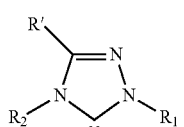

[Chemical Formula B-5]

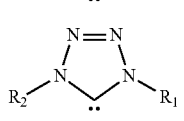

[Chemical Formula B-6]

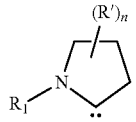

[Chemical Formula B-7]

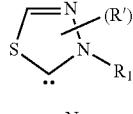

[Chemical Formula B-8]

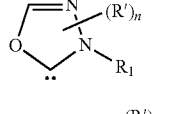

[Chemical Formula B-9]

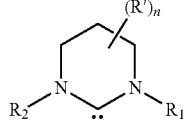

[Chemical Formula B-10]

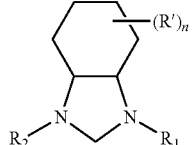

[Chemical Formula B-11]

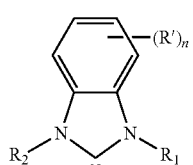

[Chemical Formula B-12]

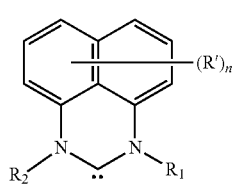

[Chemical Formula B-13]

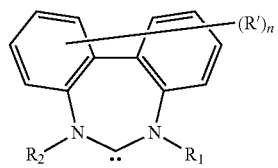

wherein R1 and R2 are each as defined above,

R' is selected from among a hydrogen atom, a deuterium atom, a halogen, a substituted or unsubstituted alkyl of 1 to 30 carbon atoms, a substituted or unsubstituted aryl of 6 to 50 carbon atoms, a substituted or unsubstituted arylalkyl of 7 to 50 carbon atoms, a substituted or unsubstituted cycloalkyl of 3 to 30 carbon atoms, a substituted or unsubstituted alkoxy of 1 to 30 carbon atoms, a substituted or unsubstituted aryloxy of 6 to 30 carbon atoms, a substituted or unsubstituted heteroaryl of 2 to 50 carbon atoms bearing O, N, or S as a heteroatom, n is an integer of 1 to 8, and when plural R's exist in one molecule, R's may be the same or different.

For instance, the N-heterocyclic carbene may be one selected from among the following Chemical Formulas B-20 to B-37:

[Chemical Formula B-20]

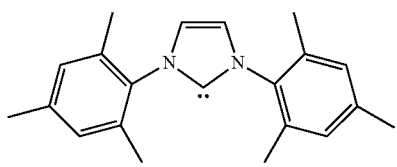

[Chemical Formula B-21]

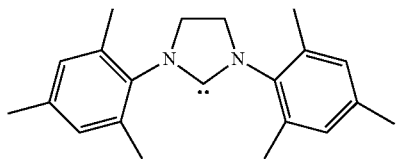

[Chemical Formula B-22]

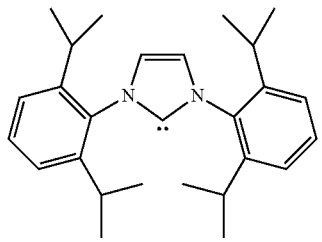

[Chemical Formula B-23]

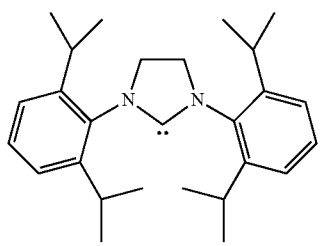

[Chemical Formula B-24]

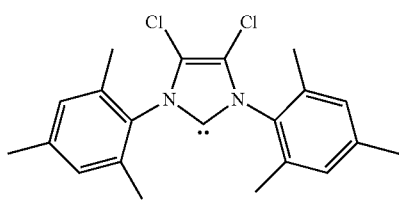

[Chemical Formula B-25]

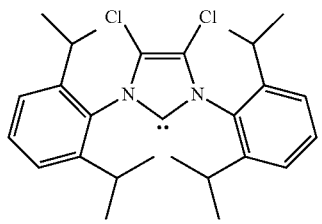

[Chemical Formula B-26]

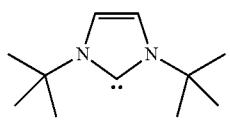

[Chemical Formula B-27]

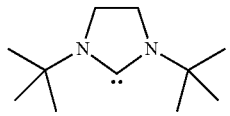

[Chemical Formula B-28]

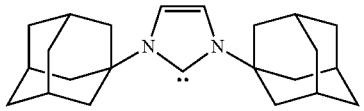

[Chemical Formula B-29]

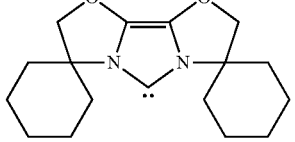

[Chemical Formula B-30]

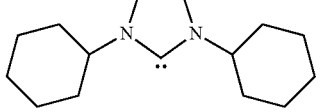

[Chemical Formula B-31]

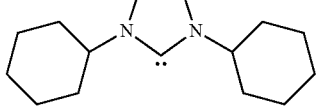

[Chemical Formula B-32]

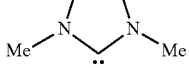

[Chemical Formula B-33]

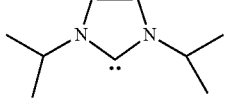

[Chemical Formula B-34]

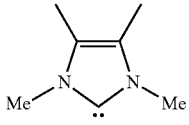

[Chemical Formula B-35]

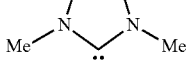

[Chemical Formula B-36]

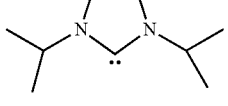

[Chemical Formula B-37]

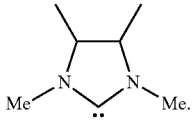

The transition metal M available in the transition metal complex according to the present disclosure may be selected from among ruthenium, iron, cobalt, rhodium, iridium, osmium, molybdenum, and tungsten, with preference for ruthenium, osmium, rhodium, and iridium and greater preference for ruthenium.

So long as it is represented by Chemical Formula A, any compound is available as the transition metal complex of the present disclosure irrespective of kinds thereof. In a particular embodiment, a halide of the transition metal complex is used.

The ligands L2 and L3, which are used, in addition to the phosphine or N-heterocyclic carbene (NHC) ligand and the sulfonamide or amide ligand, within the transition metal complex represented by Chemical Formula A, may be each a monovalent ligand or a neutral ligand. In this regard, kinds and numbers of L2 and L3 may be determined depending on the kind or oxidation number of the metal. For example, L2 and L3 may be an appropriate number of monovalent ligands and neutral ligands alone or in combination and may coordinate to the central metal. L2 and L3 may be connected to each other to form a ring with M. Further, when L2 or L3 are plural, the corresponding L2's or L3's may be connected to each other to form a ring with M.

In the complex catalyst represented by Chemical Formula A according to one embodiment of the present disclosure, L2 and L3 may be the same or different and are each independently a halogen selected from among F, Cl, Br, and I, and n and m may each be 1.

In the complex catalyst represented by Chemical Formula A according to a particular embodiment of the present disclosure, the transition metal M is ruthenium, and when n and m are each 1, the ligands L2 and L3 may each be Cl.

Further, the present disclosure provides a method for preparing a transition metal complex represented by Chemical Formula A, the method comprising contacting a transition metal complex as a reactant with a double bond-containing sulfonamide or a double bond-containing amide wherein the reactant transition metal complex contains an N-heterocyclic carbene ligand; or a phosphine ligand containing a substituted or unsubstituted alkyl of 1 to 30 carbon atoms or a substituted or unsubstituted aryl of 6 to 30 carbon atoms; plus an additional carbene ligand; and does neither contain sulfonamide nor amide as a ligand, and the double bond-containing sulfonamide or double bond-containing amide is substituted for the additional carbene in the transition metal complex to afford the transition metal complex represented by Chemical Formula A.

In this context, the sulfonamide or amide may be a compound in which the nitrogen atom has a vinyl group as a double bond attached thereto.

The method for preparing a transition metal complex represented by Chemical Formula A according to the present disclosure may be expressed as shown in the following Reaction Scheme 1:

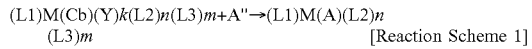
[Reaction Scheme 1]

wherein M, L1, L2, L3, m, n, and A are each as defined above,

A" is an amide having a substituent, inclusive of a vinyl group, attached thereto, and Cb is a carbene ligand represented by the following Structural Formula M:

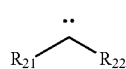
[Structural Formula M]

wherein R21 and R22, which may be the same or different, are each independently selected from among a hydrogen atom, a deuterium atom, a halogen, a cyano, a substituted or unsubstituted alkyl of 1 to 30 carbon atoms, a substituted or unsubstituted aryl of 6 to 50 carbon atoms, a substituted or unsubstituted arylalkyl of 7 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, and a substituted or unsubstituted heteroaryl of 2 to 50 carbon atoms bearing O, N, or S as a heteroatom, Y is a monovalent ligand selected from among a hydrogen atom, a deuterium atom, a halogen, a cyano, a substituted or unsubstituted alkyl of 1 to 30 carbon atoms, a substituted or unsubstituted aryl of 6 to 50 carbon atoms, a substituted or unsubstituted arylalkyl of 7 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted heteroaryl of 2 to 50 carbon atoms bearing O, N, or S as a heteroatom, a substituted or unsubstituted carboxylate anion of 1 to 30 carbon atoms, and a nitrate (NO3-), or a neutral ligand selected from among a phosphine containing a substituted or unsubstituted alkyl of 1 to 30 carbon atoms or substituted or unsubstituted aryl of 6 to 50 carbon atoms, carbon monoxide, an amine containing a substituted or unsubstituted alkyl of 1 to 30 carbon atoms or a substituted or unsubstituted aryl of 6 to 50 carbon atoms, a nitrile containing a substituted or unsubstituted alkyl of 1 to 30 carbon atoms or a substituted or unsubstituted aryl of 6 to 50 carbon atoms, and a substituted or unsubstituted aromatic heterocyclic compound of 2 to 50 carbon atoms bearing O, N, or S as a heteroatom; and k is an integer of 1 or 2 and when k is 2, the corresponding Y's may be the same or different.

That is, the transition metal complex such as the structure of Chemical Formula A contains an N-heterocyclic carbene ligand; or a phosphine ligand; and a sulfonamide or amide ligand. In this context, the transition metal complex represented by Chemical Formula A may be prepared by a substitution reaction between a transition metal complex containing an N-heterocyclic carbene ligand or phosphine ligand, but neither sulfonamide nor amide, and a double bond-containing sulfonamide or amide.

As for reaction conditions, solvents and reaction temperatures available in ligand substitution reactions for ordinary transition metal complexes can be employed. Halides of transition metals and particularly a copper halide may be used to promote the reaction.

For example, copper (I) chloride may be used for the ligand substitution reaction.

As a solvent available for the ligand substitution reaction, a person skilled in the art can properly use one selected from among a hydrocarbon, a halogenated hydrocarbon, an alcohol, an ether, a cyclic ether, a ketone, an amide, and a combination thereof. The reaction temperature may be determined according to the solvent and reactants used, and may range from 0 to 200° C. and particularly from room temperature (25° C.) to 100° C.

In accordance with another embodiment of the present disclosure, when L1 is an N-heterocyclic carbene ligand in Chemical Formula A, the transition metal complex may be prepared by subjecting a transition metal complex represented by Chemical Formula A wherein L1 is a phosphine ligand containing a substituted or unsubstituted alkyl of 1 to 30 carbon atoms or a substituted or unsubstituted aryl of 6 to 30 carbon atoms to a ligand exchange reaction with an N-heterocyclic carbene ligand.

This method corresponds to a method for preparing a transition metal complex represented by Chemical Formula A wherein L1 is an N-heterocyclic carbene ligand, the method comprising contacting a transition metal complex as a reactant with an N-heterocyclic carbene ligand, the reactant transition metal complex including a phosphine ligand containing a substituted or unsubstituted alkyl of 1 to 30 carbon atoms or a substituted or unsubstituted aryl of 6 to 30 carbon atoms, but not an N-heterocyclic carbene ligands; and containing sulfonamide or amide as a ligand, to substitute the N-heterocyclic carbene ligand for the phosphine ligand containing a substituted or unsubstituted alkyl of 1 to 30 carbon atoms or a substituted or unsubstituted aryl of 6 to 30 carbon atoms in the transition metal complex to afford the transition metal complex represented by Chemical Formula A wherein L1 is an N-heterocyclic carbene ligand.

In greater detail, a method for preparing a transition metal complex containing a sulfonamide or amide as a ligand plus an N-heterocyclic carbene ligand can be accounted by the following Reaction Scheme 2:

(P)M(A)(L2)$n$(L3)$m$+NHC→(NHC)M(A)(L2)$n$(L3)$m$ [Reaction Scheme 2]

wherein M, L2, L3, m, n, and A are as defined above,

P is a phosphine ligand containing a substituted or unsubstituted alkyl of 1 to 30 carbon atoms or a substituted or unsubstituted aryl of 6 to 30 carbon atoms, and NHC means an N-heterocyclic carbene ligand.

By way of example, when the transition metal (M) is ruthenium and A is a sulfonamide containing substituents R11 to R13, Reaction Scheme 2 may be illustrated as follows:

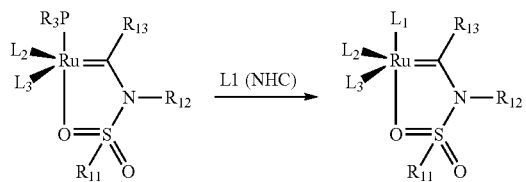

wherein L1 is an N-heterocyclic carbene ligand, PR3 is a phosphine ligand containing a substituted or unsubstituted alkyl of 1 to 30 carbon atoms or a substituted or unsubstituted aryl of 6 to 30 carbon atoms, and m and n are each 1.

In addition, the present disclosure provides a method for conducting an olefin metathesis reaction by using a transition metal complex containing a sulfonamide or amide as a ligand as a catalyst.

Further, the present disclosure provides a catalyst for an olefin metathesis reaction, the catalyst being prepared by supporting a transition metal complex containing a sulfonamide or amide as a ligand on a carrier.

For example, the olefin metathesis reaction may be an olefin ring-closing metathesis reaction.

In this regard, the catalyst of the present disclosure may be used in an amount corresponding to 0.1 to 30 mol % and particularly 1 to 20 mol % of the transition metal complex, based on the mole of the olefin reactant.

The olefin metathesis reaction using the complex catalyst or supported catalyst may be conducted in a solvent. As the solvent, a person skilled in the art can properly use one selected from among a hydrocarbon, a halogenated hydrocarbon, an alcohol, an ether, a cyclic ether, a ketone, an amide, and a combination thereof.

The reaction temperature may be determined according to the solvent and reactants used and may range from 0 to 200° C. and particularly from room temperature (25° C.) to 100° C.

In addition, the present disclosure provides a catalyst, represented by the following [Chemical Formula D], for an olefin metathesis reaction:

(L1)M(B)(L2)$n$(L3)$m$     [Chemical Formula D]

wherein,

M is a transition metal,

L1 means a phosphine ligand containing a substituted or unsubstituted alkyl of 1 to 30 carbon atoms or a substituted or unsubstituted aryl of 6 to 30 carbon atoms, or an N-heterocyclic carbene ligand, L2 and L3, which may be the same or different, are each independently a monovalent ligand selected from among a hydrogen atom, a deuterium atom, a halogen, a cyano, a substituted or unsubstituted alkyl of 1 to 30 carbon atoms, a substituted or unsubstituted aryl of 6 to 50 carbon atoms, a substituted or unsubstituted arylalkyl of 7 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 2 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted arylthioxy of 6 to 30 carbon atoms, a substituted or unsubstituted alkylthioxy of 1 to 30 carbon atoms, a substituted or unsubstituted heteroaryl of 2 to 50 carbon atoms bearing O, N, or S as a heteroatom, a substituted or unsubstituted carboxylate anion of 1 to 30 carbon atoms, and a nitrate (NO3-); or a neutral ligand selected from among a phosphine containing a substituted or unsubstituted alkyl of 1 to 30 carbon atoms or a substituted or unsubstituted aryl of 6 to 50 carbon atoms, carbon monoxide, an amine containing a substituted or unsubstituted alkyl of 1 to 30 carbon atoms or a substituted or unsubstituted aryl of 6 to 50 carbon atoms, a nitrile containing a substituted or unsubstituted alkyl of 1 to 30 carbon atoms or a substituted or unsubstituted aryl of 6 to 50 carbon atoms, and a substituted or unsubstituted aromatic heterocyclic compound of 2 to 50 carbon atoms bearing O, N, or S as a heteroatom;

in the alterative for L2 and L3, L2 and L3 may be connected to each other to form a ring with M, and when L2 and L3 are each plural, the plural L2's or L3's may be connected to each other to form a ring with M, n and m, which may be the same or different, are each independently an integer of 0 to 2 and when n or m is 2, the corresponding L2's or L3's may be the same or different, and B is represented by A'-P, wherein A' is a radical resulting from removal of one of hydrogens bound to carbon atoms in a sulfonamide or amide group, P is a carrier radical resulting from removal of one hydrogen from an intact carrier thereof, and A' and P form a covalent bond via which the carrier is connected to the sulfonamide or amide.

Here, the carrier of the catalyst, represented by Chemical Formula D, for olefin metathesis may be at least one selected from among alumina, silica, and a polymer.

A better understanding of the present disclosure may be obtained through the following examples which are set forth to illustrate, but are not to be construed as limiting the present disclosure.

EXAMPLES

Below, a detailed description will be given of a method for preparing a transition metal complex according to some embodiments of the present disclosure.

Compounds prepared according to the method of the present disclosure, such as ligands, complexes, etc., were analyzed by NMR spectroscopy, X-ray crystallography, and elemental analysis. When synthesized, compounds were measured for yield (%) by NMR.

To obtain NMR spectra, 1H NMR analysis was made using Bruker DPX300, AMX400, Agilent 400-MR, JEOL ECA400, or JEOL ECA400SL. In this regard, a suitable amount of the transition metal complex obtained was transferred from a glove box to an NMR tube while CD2C12 or benzene-d6 was used as a solvent.

Preparation of Transition Metal Complex Containing Sulfonamide Ligand

Preparation Example 1

Synthesis of (1,3-bis(2,4,6-trimethylphenyl)-2-imidazolidinylidine)dichloro(N-methylene-N-phenyl-methanesulfonamide)ruthenium

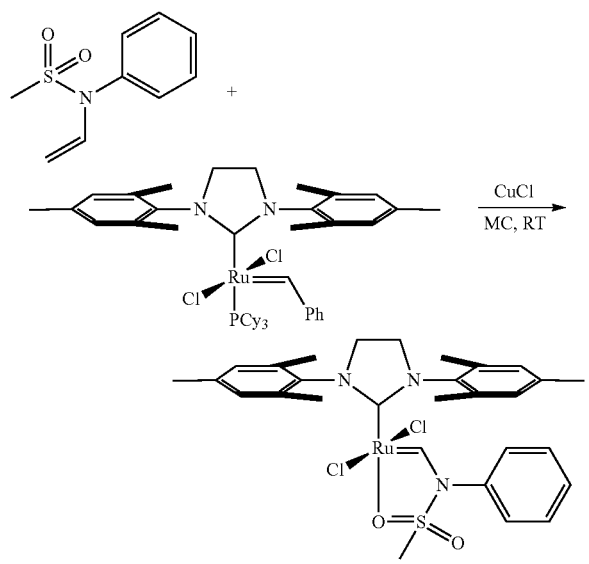

In an oxygen- and moisture-free glove box, (1,3-bis(2,4,6-trimethylphenyl)-2-imidazolidinylidine)dichloro(phenylmethylene) (tricyclohexylphosphine)ruthenium (84.90 mg, 0.1 mmol), N-phenyl-N-vinylmethanesulfonamide (39.45 mg, 0.2 mmol), copper (I) chloride (19.80 mg, 0.2 mmol), and dichloromethane (4 ml) were added to a 25 ml Schlenk glass tube.

After the lid thereof was sealed with a rubber septum, the Schlenk glass tube was withdrawn from the glove box and sealed with Parafilm. Subsequently, the glass tube was agitated at room temperate for 3 hours. After completion of the reaction, the reaction mixture was separated by silica chromatography using a mixture of dichloromethane and methanol as a mobile phase to obtain the product of interest, (1,3-bis(2,4,6-trimethylphenyl)-2-imidazolidinylidine)dichloro(N-methylene-N-phenylmethanesulfonamide)ruthenium.

NMR: 1H NMR (500 MHz, CD2C12) δ=13.11 (s, 1H), 7.51 (t, J=8.0 Hz 1H), 7.43 (t, J=8.0 Hz, 2H), 7.01~6.64 (m, 4H), 4.11 (s, 4H), 3.22 (s, 3H), 2.57~1.92 (m, 18H)

Preparation Example 2

Synthesis of <(1,3-bis(2,4,6-trimethylphenyl)-2-imidazolidinylidine)dichloro(N-(4-methoxyphenyl)-N-methylenemethanesulfonamide)ruthenium>

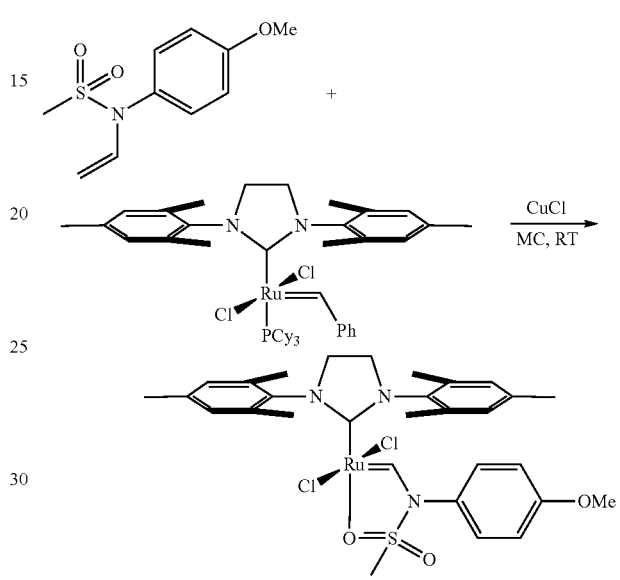

(1,3-Bis(2,4,6-trimethylphenyl)-2-imidazolidinylidine) dichloro(phenylmethylene) (tricyclohexylphosphine)ruthenium (84.90 mg, 0.1 mmol), N-(4-methoxyphenyl)-N-vinylmethanesulfonamide (45.46 mg, 0.2 mmol), copper (I) chloride (19.80 mg, 0.2 mmol), and dichloromethane (4 ml) were reacted in the same condition as in Preparation Example 1 to afford (1,3-bis(2,4,6-trimethylphenyl)-2-imidazolidinylidine)dichloro(N-(4-methoxyphenyl)-N-methylenemethanesulfonamide)ruthenium.

NMR: 1H NMR (500 MHz, C6D6) δ=13.17 (s, 1H), 6.71 (d, J=9.2 Hz, 2H), 6.44 (d, J=8.6 Hz, 2H), 6.92~6.39 (m, 4H), 3.39 (s, 4H), 3.20 (s, 3H), 2.83~2.37 (m, 12H), 2.61 (s, 3H), 2.19~1.70 (m, 6H) ppm

Preparation Example 3

Synthesis of <(1,3-bis(2,4,6-trimethylphenyl)-2-imidazolidinylidine)dichloro(N-(3,5-bis(trifluoromethyl)phenyl)-N-methylenemethanesulfonamide) ruthenium>

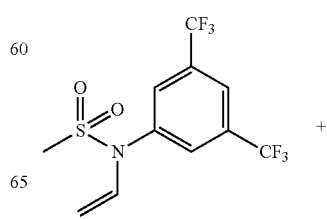

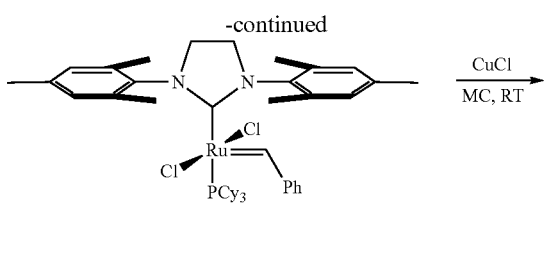

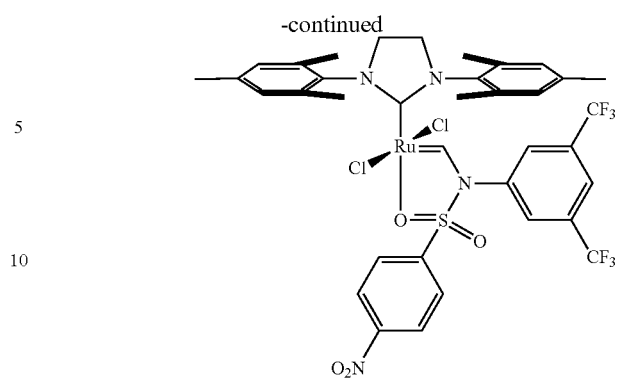

(1,3-Bis(2,4,6-trimethylphenyl)-2-imidazolidinylidine) dichloro(phenylmethylene) (tricyclohexylphosphine)ruthenium (84.90 mg, 0.1 mmol), N-(3,5-bis(trifluoromethyl)phenyl)-4-nitro-N-vinylbenzene sulfonamide (88.06 mg, 0.2 mmol), copper (I) chloride (19.80 mg, 0.2 mmol), and dichloromethane (4 ml) were reacted in the same condition as in Preparation Example 1 to afford (1,3-bis(2,4,6-trimethylphenyl)-2-imidazolidinylidine)dichloro(N-(3,5-bis(trifluoromethyl)phenyl)-N-methylene-4-nitrobenzenesulfonamide)ruthenium. Yield: 60%

Preparation Example 5

Synthesis of <(1,3-bis(2,4,6-trimethylphenyl)-2-imidazolidinylidine)dichloro(N-benzyl-N-methylenemethanesulfonamide)ruthenium>

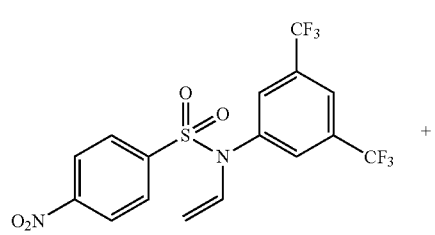

(1,3-Bis(2,4,6-trimethylphenyl)-2-imidazolidinylidine) dichloro(phenylmethylene) (tricyclohexylphosphine)ruthenium (84.90 mg, 0.1 mmol), N-(3,5-bis(trifluoromethyl)phenyl)-N-vinylmethanesulfonamide (66.65 mg, 0.2 mmol), copper (I) chloride (19.80 mg, 0.2 mmol), and dichloromethane (4 ml) were reacted in the same condition as in Preparation Example 1 to afford (1,3-bis(2,4,6-trimethylphenyl)-2-imidazolidinylidine)dichloro(N-(3,5-bis(trifluoromethyl)phenyl)-N-methylenemethanesulfonamide)ruthenium. Yield: 70%

NMR: 1H NMR (500 MHz, C6D6) δ=13.27 (s, 1H), 7.67 (s, 1H), 7.33 (s, 2H), 6.72 (brs, 4H), 3.42 (s, 4H), 2.50 (bs, 12H), 2.4 (s, 3H), 1.85 (bs, 6H) ppm Preparation Example 4

Synthesis of <(1,3-bis(2,4,6-trimethylphenyl)-2-imidazolidinylidine)dichloro(N-(3,5-bis(trifluoromethyl)phenyl)-N-methylene-4-nitrobenzenesulfonamide)ruthenium>

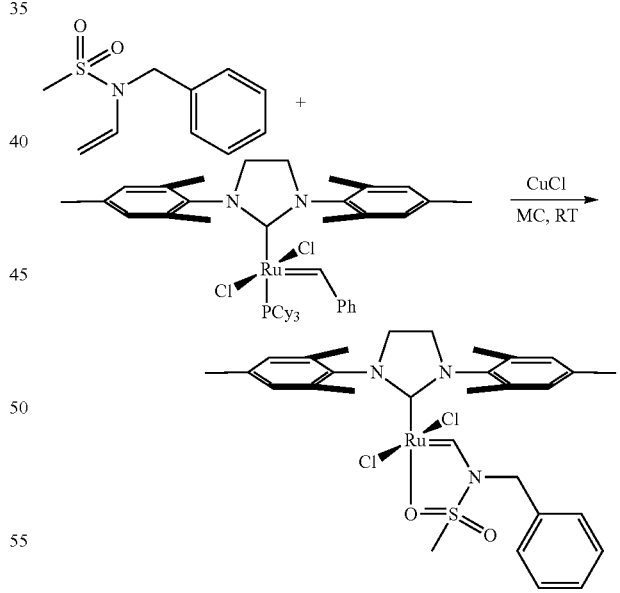

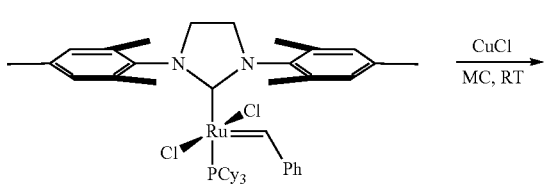

(1,3-Bis(2,4,6-trimethylphenyl)-2-imidazolidinylidine) dichloro(phenylmethylene) (tricyclohexylphosphine)ruthenium (84.90 mg, 0.1 mmol), N-benzyl-N-vinylmethanesulfonamide (42.26 mg, 0.2 mmol), copper (I) chloride (19.80 mg, 0.2 mmol), and dichloromethane (4 ml) were reacted in the same condition as in Preparation Example 1 to afford (1,3-bis(2,4,6-trimethylphenyl)-2-imidazolidinylidine)dichloro(N-benzyl-N-methylenemethanesulfonamide)ruthenium. Yield: 83%

NMR: 1H NMR (500 MHz, CD2Cl2) δ=13.14 (s, 1H), 7.41 (d, J=5.7 Hz, 3H), 7.02 (d, J=7.0 Hz, 2H), 7.17~6.58 (m, 4H), 4.73 (d, J=17.4 Hz, 1H), 4.56 (d, J=16.0 Hz, 1H), 4.11 (s, 4H), 3.05 (s, 3H), 2.72~1.99 (m, 18H) ppm Preparation Example 6

Synthesis of <(1,3-bis(2,4,6-trimethylphenyl)-2-imidazolidinylidine)dichloro(N-(4-methoxybenzyl)-N-methylenemethanesulfonamide)ruthenium>

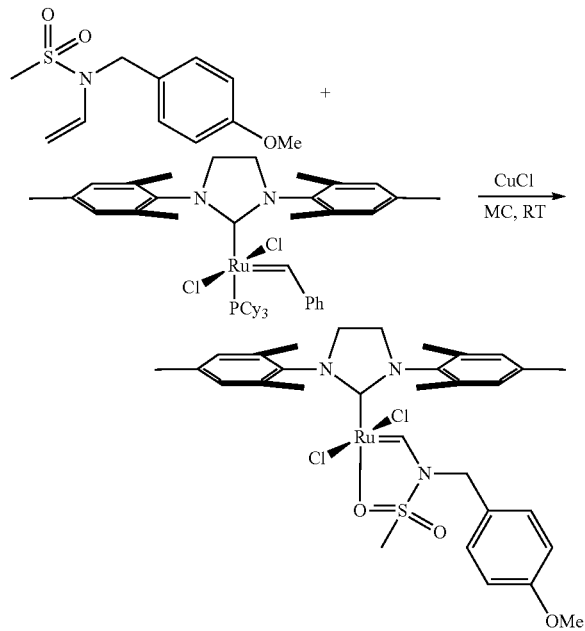

(1,3-Bis(2,4,6-trimethylphenyl)-2-imidazolidinylidine) dichloro(phenylmethylene) (tricyclohexylphosphine)ruthenium (84.90 mg, 0.1 mmol), N-(4-methoxybenzyl)-N-vinylmethanesulfonamide (48.26 mg, 0.2 mmol), copper (I) chloride (19.80 mg, 0.2 mmol), and dichloromethane (4 ml) were reacted in the same condition as in Preparation Example 1 to afford (1,3-bis(2,4,6-trimethylphenyl)-2-imidazolidinylidine)dichloro(N-(4-methoxybenzyl)-N-methylenemethanesulfonamide)ruthenium. Yield: >99%

NMR: 1H NMR (500 MHz, CD2Cl2) δ=13.17 (s, 1H), 7.09~6.64 (m, 8H), 4.68 (d, J=16.8 Hz, 1H), 4.46 (d, J=16.3 Hz, 1H), 4.12 (s, 4H), 3.85 (s, 3H), 2.98 (s, 3H), 2.69~2.00 (m, 18H) ppm Preparation Example 7

Synthesis of <(1,3-bis(2,4,6-trimethylphenyl)-2-imidazolidinylidine)dichloro(N-methylene-N-(4-nitrobenzyl)methanesulfonamide)ruthenium>

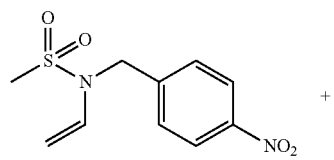

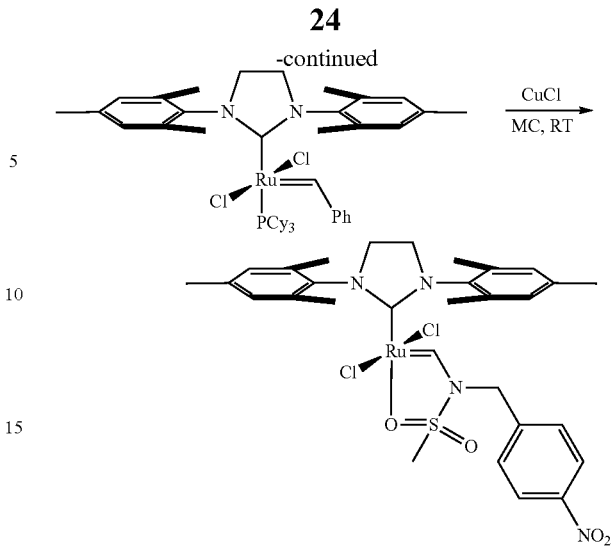

(1,3-Bis(2,4,6-trimethylphenyl)-2-imidazolidinylidine) dichloro(phenylmethylene) (tricyclohexylphosphine)ruthenium (84.90 mg, 0.1 mmol), N-(4-nitrobenzyl)-N-vinylmethanesulfonamide (51.26 mg, 0.2 mmol), copper (I) chloride (19.80 mg, 0.2 mmol), and dichloromethane (4 ml) were reacted in the same condition as in Preparation Example 1 to afford (1,3-bis(2,4,6-trimethylphenyl)-2-imidazolidinylidine)dichloro(N-methylene-N-(4-nitrobenzyl) methanesulfonamide)ruthenium.

NMR: 1H NMR (500 MHz, CD2Cl2) δ=13.10 (s, 1H), 8.24 (d, J=8.7 Hz, 2H), 7.23 (d, J=8.1 Hz, 2H), 7.16~6.38 (m, 4H), 4.75 (d, J=17.5 Hz, 1H), 4.66 (d, J=17.0 Hz, 1H) ppm Preparation Example 8

Synthesis of <(1,3-bis(2,4,6-trimethylphenyl)-2-imidazolidinylidine)dichloro(N-(4-fluorobenzyl)-N-methylenemethanesulfonamide)ruthenium>

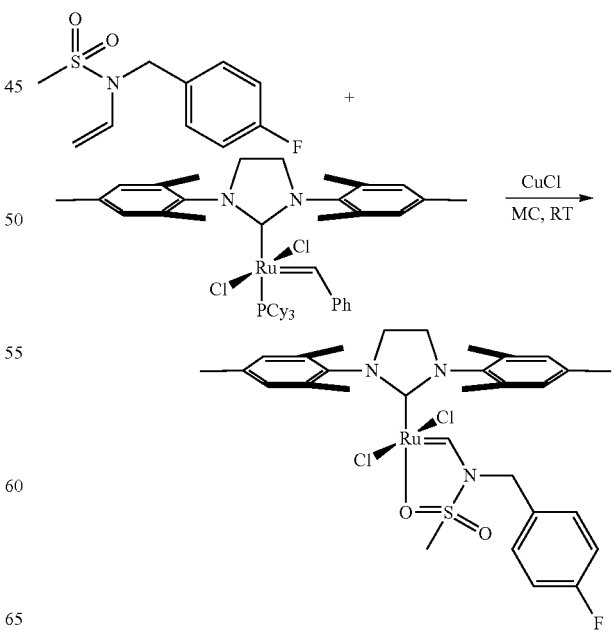

(1,3-Bis(2,4,6-trimethylphenyl)-2-imidazolidinylidine) dichloro(phenylmethylene) (tricyclohexylphosphine)ruthenium (84.90 mg, 0.1 mmol), N-(4-fluorobenzyl)-N-vinylmethanesulfonamide (45.85 mg, 0.2 mmol), copper (I) chloride (19.80 mg, 0.2 mmol), and dichloromethane (4 ml) were reacted in the same condition as in Preparation Example 1 to afford (1,3-bis(2,4,6-trimethylphenyl)-2-imidazolidinylidine)dichloro(N-(4-fluorobenzyl)-N-methylenemethanesulfonamide)ruthenium.

NMR: 1H NMR (500 MHz, CD2C12) δ=13.13 (s, 1H), 7.09 (t, J=8.4 Hz, 2H), 7.00 (t, J=7.0 Hz, 2H), 7.12~6.59 (m, 4H), 4.65 (d, J=17.0 Hz, 1H), 4.53 (d, J=17.3 Hz, 1H), 4.09 (s, 4H), 3.06 (s, 3H), 2.65~1.93 (m, 18H) ppm Preparation Example 9

Synthesis of <(1,3-bis(2,4,6-trimethylphenyl)-2-imidazolidinylidine)dichloro(N-methylene-N-(4-trifluoromethylbenzyl)methanesulfonamide)ruthenium>

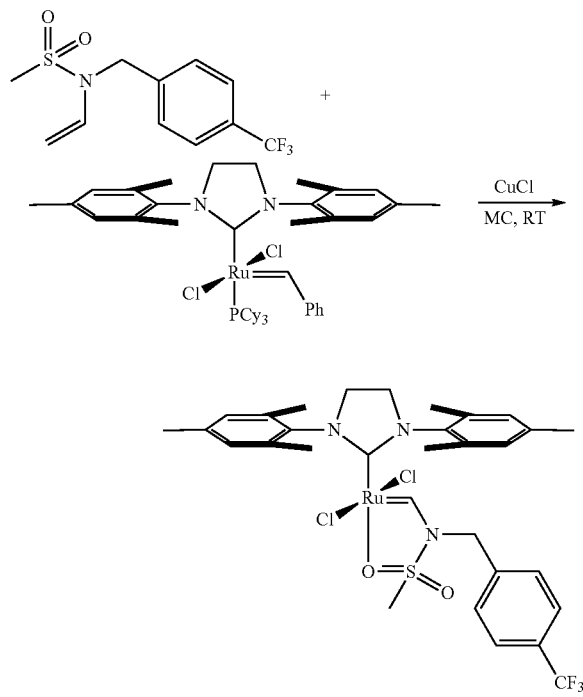

(1,3-Bis(2,4,6-trimethylphenyl)-2-imidazolidinylidine) dichloro(phenylmethylene) (tricyclohexylphosphine)ruthenium (84.90 mg, 0.1 mmol), N-(4-(trifluoromethyl)benzyl)-N-vinylmethanesulfonamide (55.86 mg, 0.2 mmol), copper (I) chloride (19.80 mg, 0.2 mmol), and dichloromethane (4 ml) were reacted in the same condition as in Preparation Example 1 to afford (1,3-bis(2,4,6-trimethylphenyl)-2-imidazolidinylidine)dichloro(N-methylene-N-(4-trifluoromethylbenzyl)methanesulfonamide)ruthenium. Yield: 83%

NMR: 1H NMR (400 MHz, CD2C12) δ=13.11 (s, 2H), 7.66 (d, J=7.6 Hz 2H), 7.15 (d, J=7.9 Hz, 2H), 7.11~6.40 (m, 4H), 4.68 (s, 2H), 4.07 (s, 4H), 3.15 (s, 3H), 24 2.69~1.90 (m, 18H) ppm 19F NMR (376 MHz, CD2C12) δ=−62.94

Preparation Example 10

Synthesis of <(1,3-bis(2,4,6-trimethylphenyl)-2-imidazolidinylidine)dichloro(N-(3,5-bistrifluoromethylbenzyl)-N-methylenemethanesulfonamide)ruthenium>

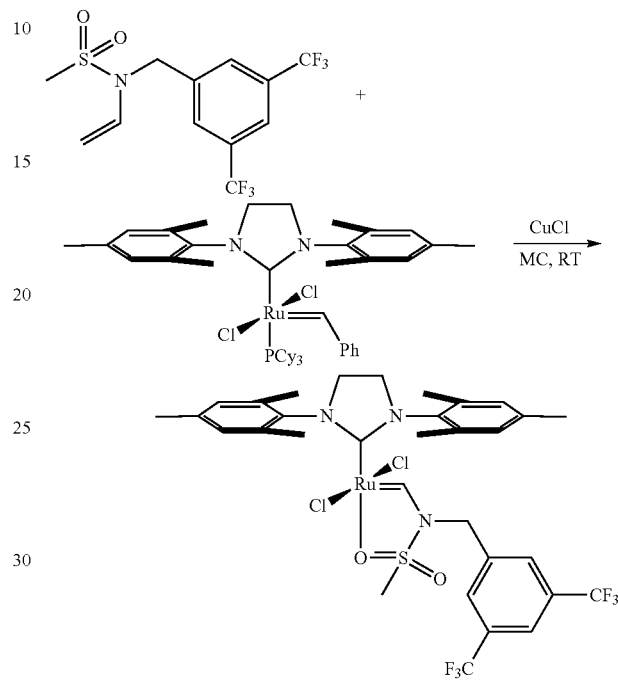

(1,3-Bis(2,4,6-trimethylphenyl)-2-imidazolidinylidine) dichloro(phenylmethylene) (tricyclohexylphosphine)ruthenium (84.90 mg, 0.1 mmol), N-(3,5-bis(trifluoromethyl)benzyl)-N-vinylmethanesulfonamide (69.46 mg, 0.2 mmol), copper (I) chloride (19.80 mg, 0.2 mmol), and dichloromethane (4 ml) were reacted in the same condition as in Preparation Example 1 to afford (1,3-bis(2,4,6-trimethylphenyl)-2-imidazolidinylidine)dichloro(N-(3,5-bis(trifluoromethyl)benzyl)-N-methylenemethanesulfonamide)ruthenium.
Yield: 78%, NMR: 1H NMR (500 MHz, CD2C12) δ=13.08 (s, 1H), 7.95 (s, 1H), 7.58 (s, 2H), 7.04 (bs, 4H), 4.72 (q, 2H), 4.12 (s, 4H), 3.21 (s, 3H), 2.72~1.99 (m 18H) ppm 19F NMR (376 MHz, CD2C12) δ=−62.88

EA: calculated: C, 47.35; H, 4.35; N, 5.18; S, 3.95 measured: C, 47.56; H, 4.70; N, 5.03; S, 3.73

Preparation Example 11

Synthesis of <(1,3-bis(2,4,6-trimethylphenyl)-2-imidazolidinylidine)dichloro(N-benzyl-4-methyl-N-methylenebenzenesulfonamide)ruthenium>

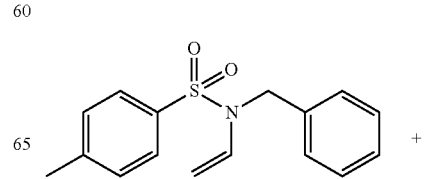

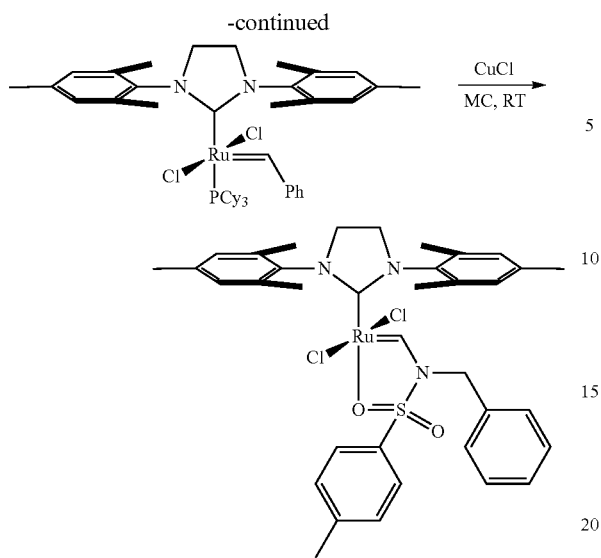

(1,3-Bis(2,4,6-trimethylphenyl)-2-imidazolidinylidine) dichloro(phenylmethylene) (tricyclohexylphosphine)ruthenium (84.90 mg, 0.1 mmol), N-benzyl-4-methyl-N-vinyl-benzenesulfonamide (57.48 mg, 0.2 mmol), copper (I) chloride (19.80 mg, 0.2 mmol), and dichloromethane (4 ml) were reacted in the same condition as in Preparation Example 1 to afford (1,3-bis(2,4,6-trimethylphenyl)-2-imidazolidinylidine)dichloro(N-benzyl-4-methyl-N-methylenebenzenesulfonamide)ruthenium. Yield: 88%, NMR: 1H NMR (500 MHz, CD2C12) δ=13.05 (s, 1H), 8.04 (s, 2H), 7.28~7.24 (m, 5H), 7.04~6.38 (m, 4H), 6.88 (s, 2H), 4.50 (d, J=17.0 Hz, 1H), 4.28 (d, J=16.7 Hz, 1H), 4.10 (s, 4H), 2.53~2.02 (m, 18H), 2.36 (s, 3H) ppm EA: calculated: C, 57.52; H, 5.50; N, 5.59; S, 4.26 measured: C, 57.83; H, 5.55; N, 5.57; S, 4.24

Preparation Example 12

Synthesis of <(1,3-bis(2,4,6-trimethylphenyl)-2-imidazolidinylidine)dichloro(N-benzyl-N-methylene-4-nitrobenzenesulfonamide)ruthenium>

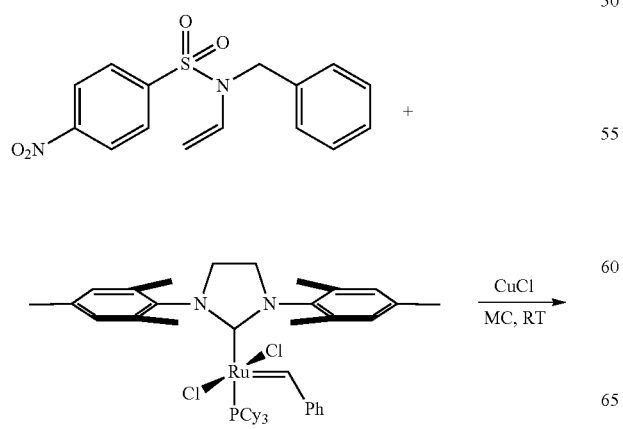

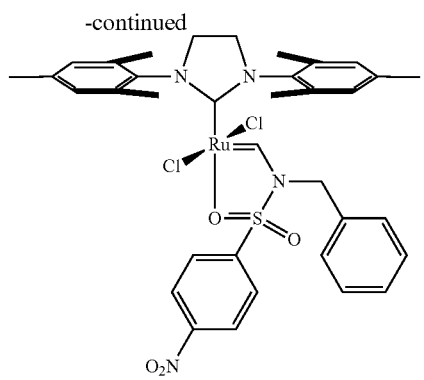

(1,3-Bis(2,4,6-trimethylphenyl)-2-imidazolidinylidine) dichloro(phenylmethylene) (tricyclohexylphosphine)ruthenium (84.90 mg, 0.1 mmol), N-benzyl-4-nitro-N-vinylbenzenesulfonamide (63.67 mg, 0.2 mmol), copper (I) chloride (19.80 mg, 0.2 mmol), and dichloromethane (4 ml) were reacted in the same condition as in Preparation Example 1 to afford (1,3-bis(2,4,6-trimethylphenyl)-2-imidazolidinylidine)dichloro(N-benzyl-N-methylene-4-nitrobenzenesulfonamide)ruthenium. Yield: 66%, NMR: 1H NMR (500 MHz, CD2C12) δ=13.11 (s, 1H), 8.39 (d, J=8.8 Hz. 2H), 8.18 (d, J=8.8 Hz, 2H), 7.27~7.23 (m, 3H), 7.046.47 (m, 4H), 6.84 (d, J=6.6 Hz, 2H), 4.52 (d, J=16.9 Hz, 1H), 4.38 (d, J=16.9 Hz, 1H), 4.13 (s, 4H), 2.53~2.07 (m, 18H) ppm EA: calculated: C, 53.71; H, 4.89; N, 7.16; S, 4.10 measured: C, 54.00; H, 4.95; N, 7.13; S, 4.06

Preparation Example 13

Synthesis of <(1,3-bis(2,4,5-trimethylphenyl)-2-imidazolidinylidine)dichloro(N-benzyl-4-methoxy-N-methylenebenzenesulfonamide)ruthenium>

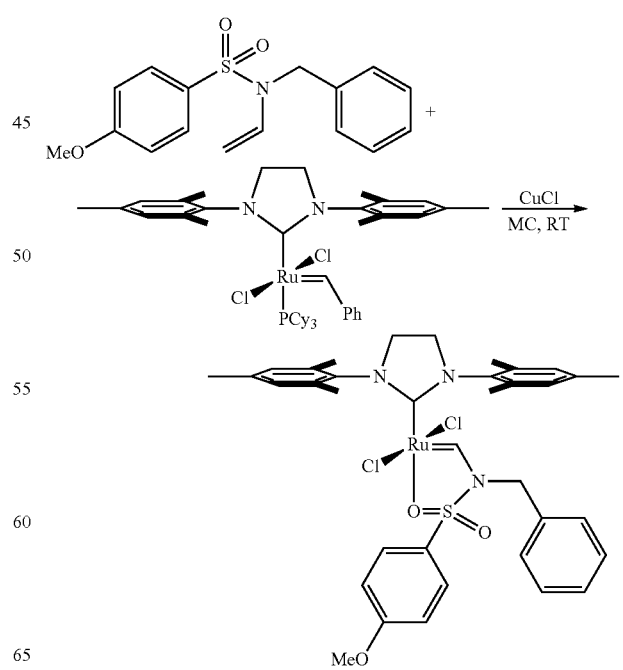

(1,3-Bis(2,4,5-trimethylphenyl)-2-imidazolidinylidine) dichloro(phenylmethylene) (tricyclohexylphosphine)ruthenium (84.90 mg, 0.1 mmol), N-benzyl-4-methoxy-N-vinylbenzenesulfonamide (60.68 mg, 0.2 mmol), copper (I) chloride (19.80 mg, 0.2 mmol), and dichloromethane (4 ml) were reacted in the same condition as in Preparation Example 1 to afford (1,3-bis(2,4,6-trimethylphenyl)-2-imidazolidinylidine)dichloro(N-benzyl-4-methoxy-N-methylenebenzenesulfonamide)ruthenium. Yield: 96%

NMR: 1H NMR (500 MHz, CD2Cl2) δ=13.01 (s, 1H), 8.09 (d, J=9.0 Hz. 2H), 7.26~7.25 (m, 3H), 7.02 (bs, 2H), 6.88 (s, 1H), 6.86~6.85 (m, 3H), 6.63 (bs, 1H), 6.37 (bs, 1H), 4.46 (d, J=17.3 Hz, 1H), 4.28 (d, J=17.2 Hz, 1H), 4.08 (s, 4H), 3.80 (s, 3H), 2.52~2.01 (m, 18H) ppm Preparation Example 14

Synthesis of <1,3-bis(2,4,6-trimethylphenyl)-2-imidazolidinylidine)dichloro(4-methoxy-N-(4-methoxybenzyl)-N-methylenebenzenesulfonamide)ruthenium>

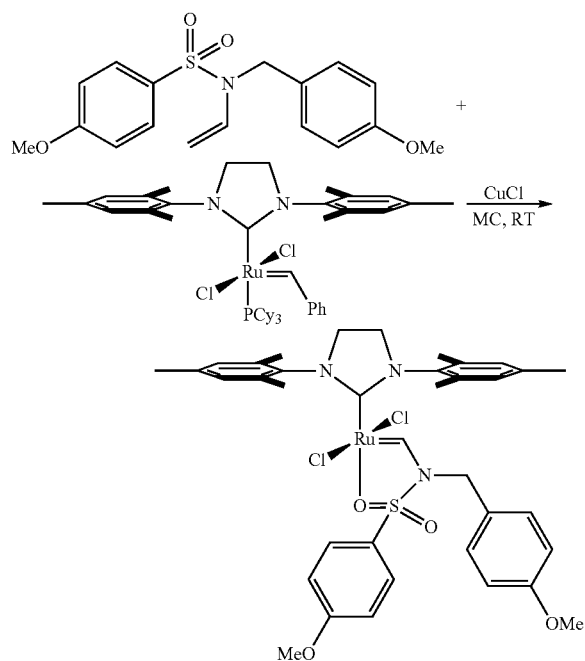

(1,3-Bis(2,4,6-trimethylphenyl)-2-imidazolidinylidine) dichloro(phenylmethylene) (tricyclohexylphosphine)ruthenium (84.90 mg, 0.1 mmol), 4-methoxy-N-(4-methoxybenzyl)-N-vinylbenzenesulfonamide (66.68 mg, 0.2 mmol), copper (I) chloride (19.80 mg, 0.2 mmol), and dichloromethane (4 ml) were reacted in the same condition as in Preparation Example 1 to afford (1,3-bis(2,4,6-trimethylphenyl)-2-imidazolidinylidine)dichloro(4-methoxy-N-(4-methoxybenzyl)-N-methylenebenzenesulfonamide) ruthenium. Yield: 99%, NMR: 1H NMR (500 MHz, CD2Cl2) δ=13.03 (s, 1H), 8.06 (d, J=8.9 Hz. 2H), 7.01 (bs, 2H), 6.86 (d, J=8.9 Hz, 2H), 6.77 (d, J=8.9 Hz, 2H), 6.74 (d, J=8.9 Hz, 2H), 6.73 (bs, 1H), 6.47 (bs, 1H), 4.38 (d, J=16.8 Hz, 1H), 4.22 (d, J=17.0 Hz, 1H), 4.08 (s, 27 4H), 3.80 (s, 6H), 2.51~2.06 (m, 18H) ppm Preparation Example 15

Synthesis of <(1,3-bis(2,4,6-trimethylphenyl)-2-imidazolidinylidine)dichloro(N-(3,5-bis(trifluoromethyl)benzyl)-3,5-bis(trifluoromethyl)-N-methylenebenzenesulfonamide)ruthenium>

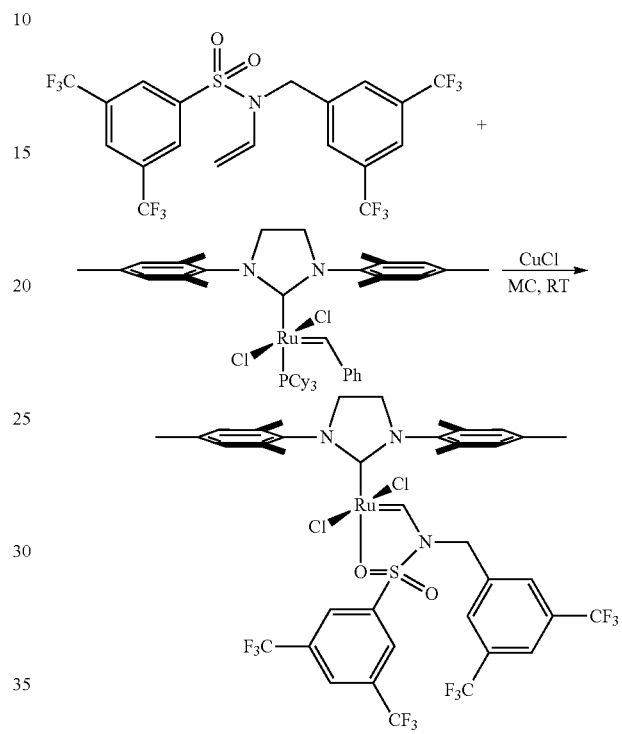

(1,3-Bis(2,4,6-trimethylphenyl)-2-imidazolidinylidine) dichloro(phenylmethylene) (tricyclohexylphosphine)ruthenium (84.90 mg, 0.1 mmol), N-(3,5-bis(trifluoromethyl) benzyl)-3,5-bis(trifluoromethyl)-N-vinylbenzenesulfonamide (109.07 mg, 0.2 mmol), copper (I) chloride (19.80 mg, 0.2 mmol), and dichloromethane (4 ml) were reacted in the same condition as in Preparation Example 1 to identify (1,3-Bis(2,4,6-trimethylphenyl)-2-imidazolidinylidine)dichloro(N-(3,5-bis(trifluoromethyl) benzyl)-3,5-bis(trifluoromethyl)-N-methylenebenzenesulfonamide)ruthenium on NMR data of the mixture solution.

Preparation Example 16

Synthesis of <(1,3-bis(2,4,6-trimethylphenyl)-2-imidazolidinylidine)dichloro(N-(2,2,2-trifluoroethyl)-N-methylenemethanesulfonamide)ruthenium>

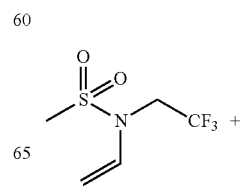

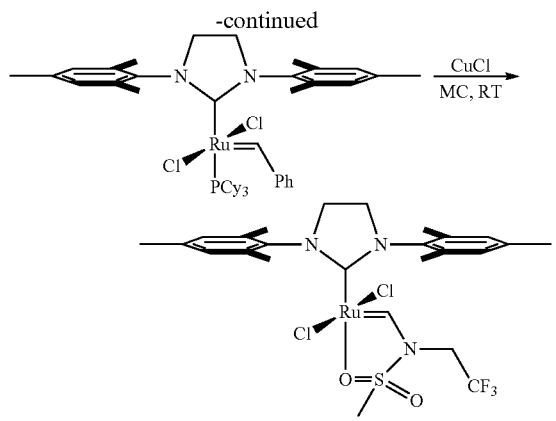

(1,3-Bis(2,4,6-trimethylphenyl)-2-imidazolidinylidine)dichloro(phenylmethylene) (tricyclohexylphosphine)ruthenium (84.90 mg, 0.1 mmol), N-(2,2,2-trifluoroethyl)-N-vinylmethanesulfonamide (40.64 mg, 0.2 mmol), copper (I) chloride (19.80 mg, 0.2 mmol), and dichloromethane (4 ml) were reacted in the same condition as in Preparation Example 1 to identify (1,3-bis(2,4,6-trimethylphenyl)-2-imidazolidinylidine)dichloro(N-(2,2,2-trifluoroethyl)-N-methylenemethanesulfonamide)ruthenium on NMR data of the mixture solution.

Preparation Example 17

Synthesis of <(1,3-bis(2,4,6-trimethylphenyl)-2-imidazolidinylidine)dichloro(N-(4-methoxyphenyl)-N-methylenetrifluoromethanesulfonamide)ruthenium

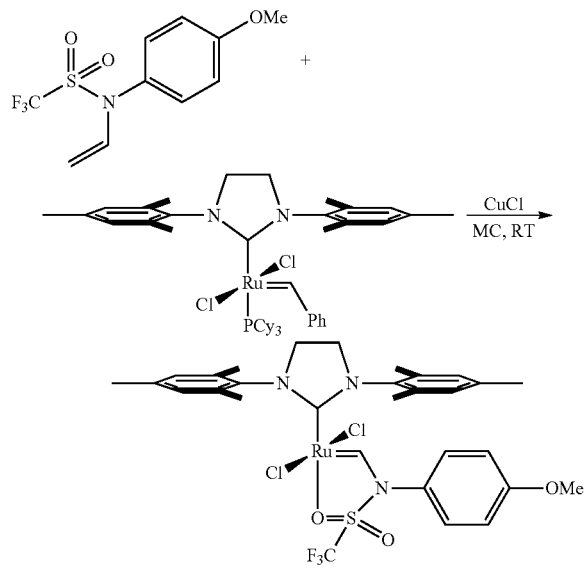

In an oxygen- and moisture-free dry box, (1,3-Bis(2,4,6-trimethylphenyl)-2-imidazolidinylidine)dichloro(phenylmethylene) (tricyclohexylphosphine)ruthenium (84.90 mg, 0.1 mmol), N-(4-methoxyphenyl)-N-vinyltrifluoromethanesulfonamide (46.25 mg, 0.1 mmol), copper (I) chloride (19.80 mg, 0.2 mmol), and dichloromethane (4 ml) were added to a 25 ml Schlenk glass tube.

After the lid thereof was sealed with a rubber septum, the Schlenk glass tube was withdrawn from the dry box and sealed with Parafilm. Subsequently, the glass tube was agitated at room temperate for 2 hours. After completion of the reaction, the reaction mixture was separated by silica chromatography using a mixture of dichloromethane and methanol as a mobile phase to obtain the product of interest, (1,3-bis(2,4,6-trimethylphenyl)-2-imidazolidinylidine)dichloro(N-(4-methoxyphenyl)-N-methylenetrifluoromethanesulfonamide)ruthenium. Yield: 60%

NMR: 1H NMR (500 MHz, CD2Cl2) δ=13.18 (s, 1H), 6.93 (d, J=8.4 Hz, 2H), 6.70 (bs, 4H), 6.88 (s, 1H), 6.44 (d, J=8.6 Hz, 2H), 3.44 (s, 4H), 3.20 (s, 3H), 2.50 (s, 12H), 1.93 (s, 6H) ppm Preparation of Transition Metal Complex Containing Amide Ligand Preparation Example 18

Synthesis of <(1,3-bis(2,4,6-trimethylphenyl)-2-imidazolidinylidine)dichloro((N-phenylacetamide)methylene)ruthenium>

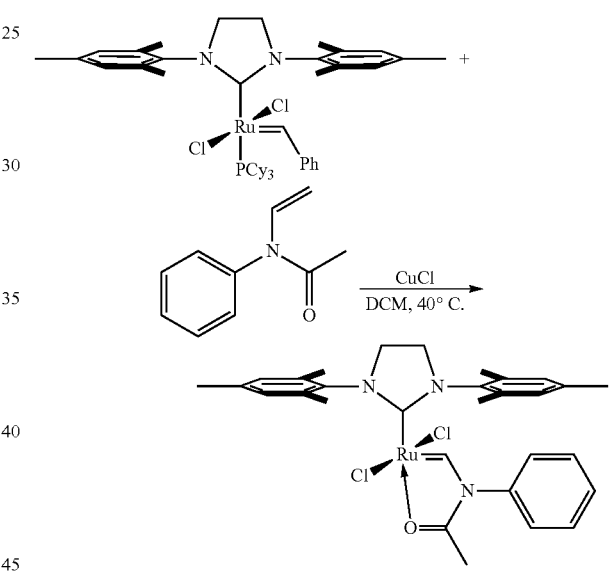

In an oxygen- and moisture-free glove box, (1,3-Bis(2,4,6-trimethylphenyl)-2-imidazolidinylidine)dichloro(phenylmethylene) (tricyclohexylphosphine)ruthenium (84.90 mg, 0.1 mmol), N-phenyl-N-vinyl acetamide (32.24 mg, 0.2 mmol), copper (I) chloride (19.80 mg, 0.2 mmol), and dichloromethane (4 ml) were added to a 25 ml Schlenk glass tube.

After a lid thereof was sealed with a rubber septum, the Schlenk glass tube was withdrawn from the glove box and additionally sealed with Parafilm. Subsequently, the glass tube was agitated at 40° C. for 12 hours. After completion of the reaction, the reaction mixture was separated by silica chromatography using a mixture of dichloromethane and methanol in an argon atmosphere to obtain the desired product (1,3-Bis(2,4,6-trimethylphenyl)-2-imidazolidinylidine)dichloro((N-phenylacetamide)methylene) ruthenium.

(Yield 60%, NMR: 1H NMR (500 MHz, C6D6) Trans isomer δ=12.51 (s, 1H), 6.87~6.82 (m, 2H), 6.71 (s, 4H), 6.70~6.65 (m, 1H), 6.45~6.43 (m, 2H), 3.43 (s, 4H), 2.64 (brs, 12H), 1.91 (brs, 6H) ppm

Preparation Example 19

Synthesis of <(1,3-bis(2,4,6-trimethylphenyl)-2-imidazolidinylidine)dichloro((N-(4-methoxyphenyl)acetamide)methylene)ruthenium>

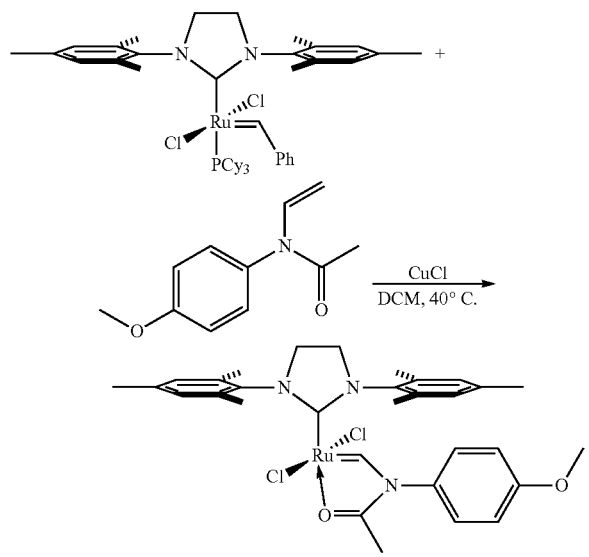

(1,3-Bis(2,4,6-trimethylphenyl)-2-imidazolidinylidine) dichloro(phenylmethylene) (tricyclohexylphosphine)ruthenium (84.90 mg, 0.1 mmol), N-(4-methoxyphenyl)-N-vinyl acetamide (38.25 mg, 0.2 mmol), copper (I) chloride (19.80 mg, 0.2 mmol), and dichloromethane (4 ml) were reacted in the same condition as in Preparation Example 18 to afford (1,3-bis(2,4,6-trimethylphenyl)-2-imidazolidinylidine)dichloro((N-(4-methoxyphenyl)acetamide)methylene)ruthenium.

(Yield 40%, NMR: 1H NMR (500 MHz, CD2C12) Cis isomer δ=13.79 (s, 1H), 7.0~6.85 (m, 6H), 6.81 (d, J=9.16, 2H), 4.29 (brs, 1H), 4.10~3.93 (m, 2H), 3.85 (s, 3H), 3.83 (brs, 1H), 2.61 (s, 3H), 2.50 (s, 3H), 2.44 (brs, 6H), 2.27 (s, 3H), 1.89 (s, 3H) ppm

Preparation Example 20

Synthesis of <(1,3-bis(2,4,6-trimethylphenyl)-2-imidazolidinylidine)dichloro((N-phenylbenzamido)methylene)ruthenium>

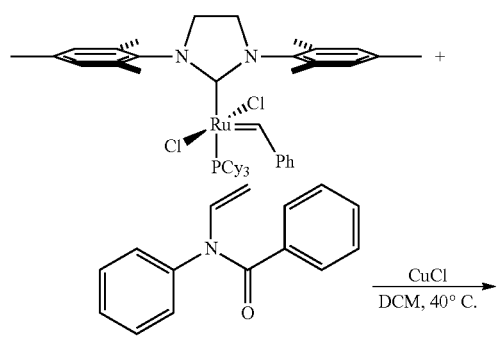

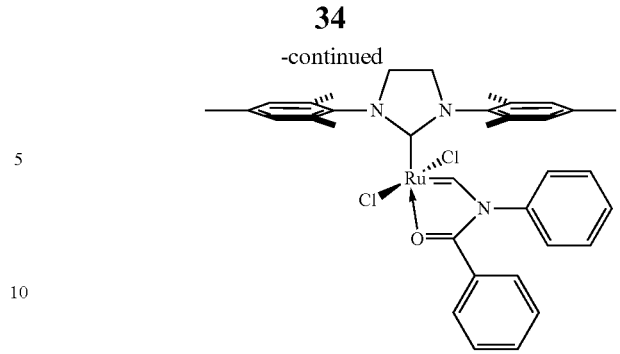

(1,3-Bis(2,4,6-trimethylphenyl)-2-imidazolidinylidine) dichloro(phenylmethylene) (tricyclohexylphosphine)ruthenium (84.90 mg, 0.1 mmol), N-phenyl-N-vinyl benzamide (44.66 mg, 0.2 mmol), copper (I) chloride (19.80 mg, 0.2 30 mmol), and dichloromethane (4 ml) were reacted in the same condition as in Preparation Example 18 to afford (1,3-bis(2,4,6-trimethylphenyl)-2-imidazolidinylidine)dichloro((N-phenylbenzamido)methylene)ruthenium.

(Yield 40%, NMR: 1H NMR (500 MHz, C6D6) Trans isomer δ=12.81 (s, 1H), 7.13 (d, J=6.85, 2H), 6.80~6.65 (m, 8H), 6.55 (m, 2H), 6.43 (d, J=8.80, 2H), 3.51 (s, 4H), 2.57 (brs, 12H), 1.94 (s, 6H) ppm

Preparation Example 21

Synthesis of <(1,3-bis(2,4,6-trimethylphenyl)-2-imidazolidinylidine)dichloro((N-(4-methoxyphenyl)-4-nitrobenzamido)methylene)ruthenium>

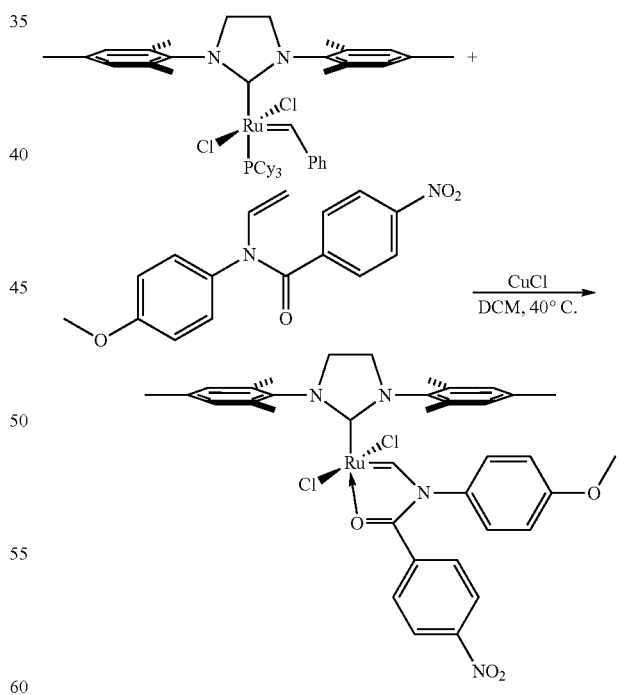

(1,3-Bis(2,4,6-trimethylphenyl)-2-imidazolidinylidine) dichloro(phenylmethylene) (tricyclohexylphosphine)ruthenium (84.90 mg, 0.1 mmol), N-(4-methoxyphenyl)-4-nitro-N-vinyl benzamide (59.66 mg, 0.2 mmol), copper (I) chloride (19.80 mg, 0.2 mmol), and dichloromethane (4 ml) were reacted in the same condition as in Preparation Example 18 to afford (1,3-bis(2,4,6-trimethylphenyl)-2-imidazolidinylidine)dichloro((N-(4-methoxyphenyl)-4-nitrobenzamido)methylene)ruthenium.

(Yield 40%, NMR: 1H NMR (500 MHz, C6D6) Trans isomer δ=12.75 (s, 1H), 7.21 (s, 2H), 6.95 (s, 2H), 6.91~6.58 (brs, 4H), 6.36 (s, 2H), 6.28 (s, 2H), 3.42 (s, 4H), 3.10 (s, 3H), 2.91~2.31 (brd, 12H), 1.98 (brs, 6H) ppm Preparation Example 22

Synthesis of <(1,3-bis(2,4,6-trimethylphenyl)-2-imidazolidinylidine)dichloro((4-nitro-N-(4-nitrophenyl)benzamido)methylene)ruthenium>

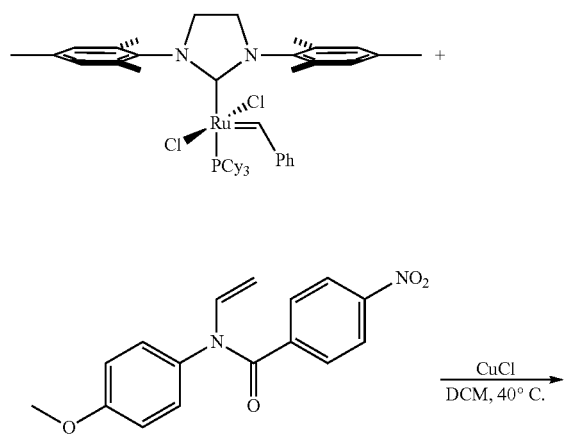

(1,3-Bis(2,4,6-trimethylphenyl)-2-imidazolidinylidine) dichloro(phenylmethylene) (tricyclohexylphosphine)ruthenium (84.90 mg, 0.1 mmol), 4-nitro-N-(4-nitrophenyl)-N-vinyl benzamide (62.65 mg, 0.2 mmol), 31 copper (I) chloride (19.80 mg, 0.2 mmol), and dichloromethane (4 ml) were reacted in the same condition as in Preparation Example 18 to afford (1,3-bis(2,4,6-trimethylphenyl)-2-imidazolidinylidine)dichloro((4-nitro-N-(4-nitrophenyl)benzamido)methylene)ruthenium.

(Yield 40%, NMR: 1H NMR (500 MHz, C6D6) Trans isomer δ=12.68 (s, 1H) 7.53 (d, J=8.70, 2H), 7.29 (s, 1H), 7.25 (d, J=9.03, 2H), 6.97 (s, 1H), 6.93~6.80 (brs, 2H), 6.74 (d, J=9.03, 2H), 6.01 (d, J=8.70, 2H), 3.37 (brs, 4H), 2.72 (brs, 6H), 2.40 (brs, 6H), 2.00 (brs, 3H), 1.83 (brs, 3H) ppm Preparation Example 23

Synthesis of <(1,3-bis(2,4,6-trimethylphenyl)-2-imidazolidinylidine)dichloro(4-nitro-N-phenylbenzamido)methylene)ruthenium>

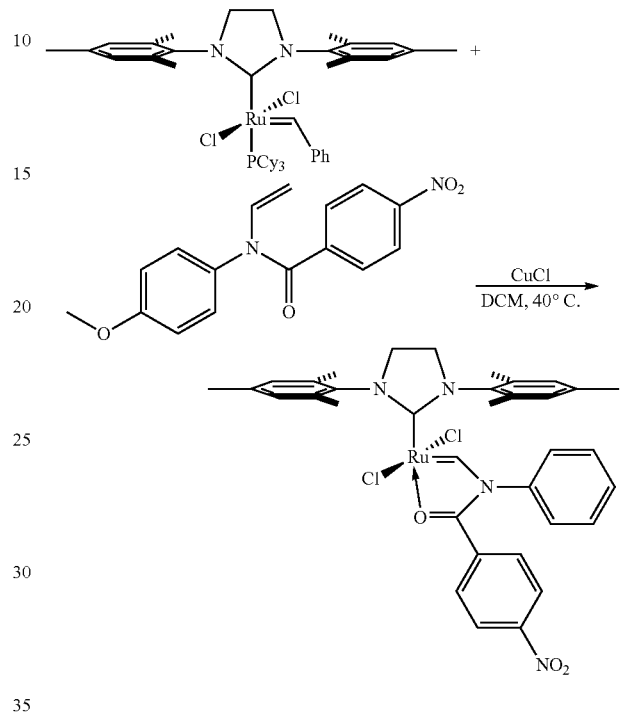

(1,3-Bis(2,4,6-trimethylphenyl)-2-imidazolidinylidine) dichloro(phenylmethylene) (tricyclohexylphosphine)ruthenium (84.90 mg, 0.1 mmol), 4-nitro-N-phenyl-N-vinyl benzamide (53.65 mg, 0.2 mmol), copper (I) chloride (19.80 mg, 0.2 mmol), and dichloromethane (4 ml) were reacted in the same condition as in Preparation Example 18 to afford (1,3-bis(2,4,6-trimethylphenyl)-2-imidazolidinylidine)dichloro(4-nitro-N-phenylbenzamido)methylene)ruthenium.

(Yield 40%, 1H NMR (500 MHz, CD2C12) Cis isomer δ=13.90 (s, 1H), 8.18 (d, J=8.37, 2H), 7.59 (d, J=8.70, 2H), 7.46~7.28 (m, 3H), 7.26 (s, 1H), 7.18 (s, 1H), 7.12 (s, 1H), 6.81 (s, 1H), 6.69 (d, J=8.03 Hz, 2H), 4.40~4.23 (brs, 1H), 4.20~3.95 (m, 2H), 3.93~3.79 (m, 1H), 2.63 (s, 3H), 2.57 (s, 3H), 2.52 (s, 3H), 2.44 (s, 3H), 2.32 (s, 3H), 1.67 (s, 3H) ppm Preparation Example 24

Synthesis of <(1,3-bis(2,4,6-trimethylphenyl)-2-imidazolidinylidine)dichloro((2,2-difluoro-N-phenylacetamide)methylene)ruthenium>

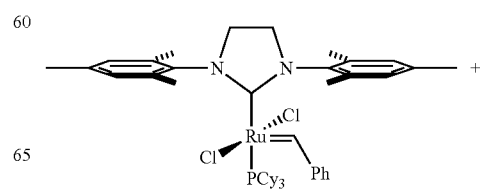

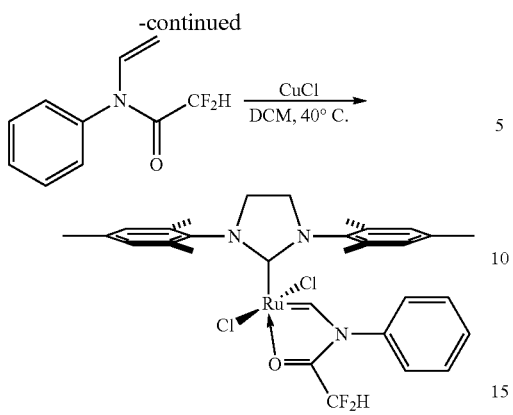

(1,3-Bis(2,4,6-trimethylphenyl)-2-imidazolidinylidine)dichloro(phenylmethylene) (tricyclohexylphosphine)ruthenium (84.90 mg, 0.1 mmol), 2,2-difluoro-N-phenyl-N-vinyl acetamide (39.44 mg, 0.2 mmol), copper (I) chloride (19.80 mg, 0.2 mmol), and dichloromethane (4 ml) were reacted in the same condition as in Preparation Example 18 to afford (1,3-bis(2,4,6-trimethylphenyl)-2-imidazolidinylidine)dichloro((2,2-difluoro-N-phenylacetamide)methylene)ruthenium.

(Yield 50%, NMR: 1H NMR (500 MHz, C6D6) Trans isomer δ=12.25 (s, 1H), 7.56~7.41 (m, 3H), 7.00 (d, J=7.83 Hz, 2H), 6.95~6.80 (brs, 4H), 6.09 (t, JH-F=52.33, 1H), 4.10 (s, 4H), 2.41 (brs, 12H), 2.12 (brs, 6H) ppm Preparation Example 25

Synthesis of <(1,3-bis(2,4,6-trimethylphenyl)-2-imidazolidinylidine)dichloro((2,2-difluoro-N-(4-methoxyphenyl)acetamide)methylene)ruthenium>

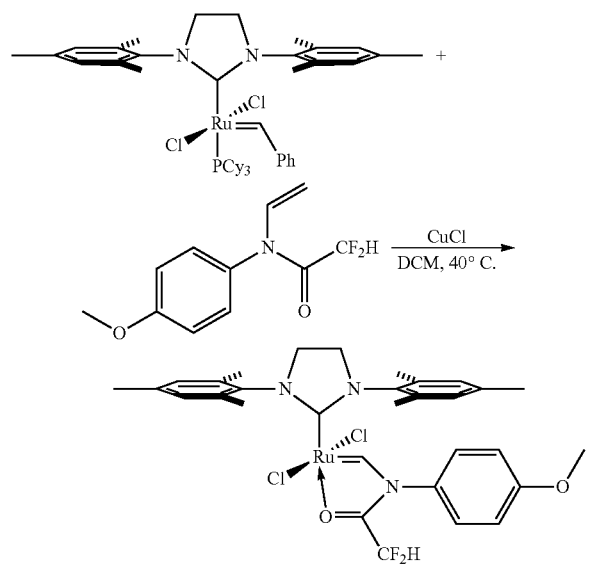

(1,3-Bis(2,4,6-trimethylphenyl)-2-imidazolidinylidine)dichloro(phenylmethylene) (tricyclohexylphosphine)ruthenium (84.90 mg, 0.1 mmol), 2,2-difluoro-N-(4-methoxyphenyl)-N-vinyl acetamide (45.44 mg, 0.2 mmol), copper (I) chloride (19.80 mg, 0.2 mmol), and dichloromethane (4 ml) were reacted in the same condition as in Preparation Example 18 to afford (1,3-bis(2,4,6-trimethylphenyl)-2-imidazolidinylidine)dichloro((2,2-difluoro-N-(4-methoxyphenyl)acetamide)methylene)ruthenium.

(Yield: 50%, NMR: 1H NMR (500 MHz, C6D6) Trans isomer δ=12.26 (s, 1H), 6.85~6.53 (brs, 4H), 6.40~6.30 (m, 4H), 6.95~6.80 (brs, 4H), 5.31 (t, JH-F=52.33, 1H), 3.34 (s, 4H), 3.10 (s, 3H), 2.52 (brs, 12H), 1.87 (brs, 6H) ppm Preparation Example 26

Synthesis of <(1,3-bis(2,4,6-trimethylphenyl)-2-imidazolidinylidine)dichloro((2,2,2-trifluoro-N-phenylacetamide)methylene)ruthenium>

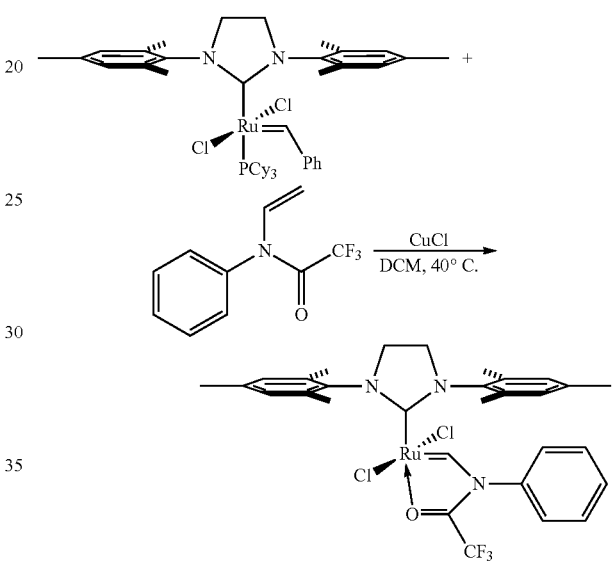

(1,3-Bis(2,4,6-trimethylphenyl)-2-imidazolidinylidine)dichloro(phenylmethylene) (tricyclohexylphosphine)ruthenium (84.90 mg, 0.1 mmol), 2,2,2-trifluoro-N-phenyl-N-vinyl acetamide (43.04 mg, 0.2 mmol), copper (I) chloride (19.80 mg, 0.2 mmol), and dichloromethane (4 ml) were reacted in the same condition as in Preparation Example 18 to afford (1,3-bis(2,4,6-trimethylphenyl)-2-imidazolidinylidine)dichloro((2,2,2-trifluoro-N-phenylacetamide)methylene)ruthenium.

(Yield 60%, NMR: 1H NMR (500 MHz, C6D6) Trans isomer δ=12.19 (s, 1H), 6.90δ6.50 (brs, 4H), 6.80 (m, 1H), 6.70 (m, 2H), 6.41 (d, J=7.94 Hz, 2H), 3.36 (s, 4H), 2.52 (brs, 12H) 1.85 (brs, 6H) ppm <Catalyst Performance Test (Ring-Closing Metathesis)>

The complex prepared according to the present disclosure was teste for activity by conducting ring-closing metathesis of diethyldiallymalonate with the catalyst.

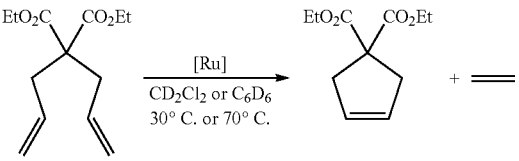

In an oxygen- and moisture-free glove box, a 0.001 mM storage solution was made of deuterium-substituted dichloromethane including the sulfonamide-containing ruthenium catalyst (0.002 mmol) or deuterium-substituted benzene including the amide-containing ruthenium catalyst (0.002 mmol) by using a 2 ml volumetric flask. Using a Hamilton syringe, 0.5 ml of the storage solution was added to an NMR tube which can be hermitically sealed.

The NMR was hermitically sealed, withdrawn from the glove box, and then additionally sealed with Parafilm.

Subsequently, diethyldiallymalonate (12.02 mg, 0.05 mmol) was added to the NMR tube. The reaction was monitored with an NMR machine preheated to 30° C. for the dichloromethane or 70° C. for the benzene. Conversion rates of the catalysts containing the sulfonamide ligand or the amide ligand are given in Tables 1 and 2, respectively. Conversion rates with time for Table 1 are depicted in FIGS. 1 (Examples 1 to 7) and 2 (Examples 8 to 13) and in FIG. 3 for Table 3.

TABLE 1

| | Catalyst | Conversion | Time |
|---|---|---|---|
| 1 | Example 1 | >90% | 93 min |
| 2 | Example 2 | >90% | 97 min |
| 3 | Example 3 | >90% | 39 min |
| 4 | Example 4 | >90% | 31 min |

TABLE 1-continued

| | Catalyst | Conversion | Time |
|---|---|---|---|
| 5 | Example 5 | >90% | 96.5 min |
| 6 | Example 6 | >80% | 120 min |
| 7 | Example 7 | >90% | 78.5 min |
| 8 | Example 8 | >90% | 93 min |

TABLE 1-continued

| | Catalyst | Conversion | Time |
|---|---|---|---|
| 9 | Example 9 | >90% | 59 min |
| 10 | Example 10 | >90% | 41.5 min |
| 11 | Example 11 | >90% | 117 min |
| 12 | Example 12 | >90% | 46.5 min |

TABLE 1-continued

| | Catalyst | Conversion | Time |
|---|---|---|---|
| 13 | Example 17 | >90% | 3 min |

Figure 2:
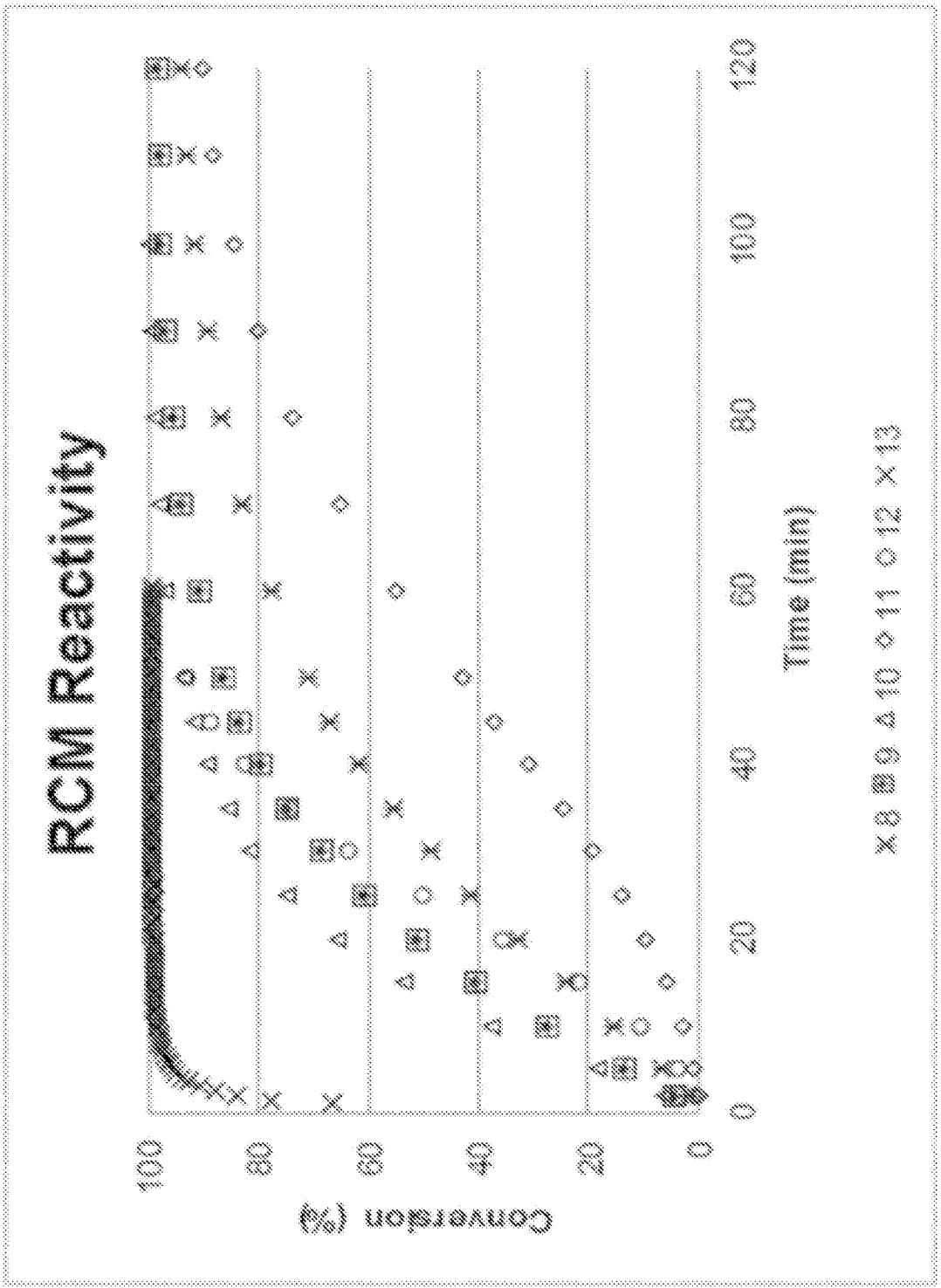
FIG. 2 depicts the activity of a catalyst containing a sulfonamide ligand prepared according to another embodiment of the present disclosure (Examples 8 to 13).

As is understood from Table 1 and FIGS. 1 and 2, the transition metal complexes according to the present disclosure exhibited a conversion rate of 80% or higher in olefin metathesis and, for the most part, a conversion rate of 90% or higher.

According to design of the sulfonamide ligand, the conversion rate over time can be easily controlled. Therefore, the complex catalyst of the present disclosure, when commercialized, has the advantage of being capable of controlling reaction behaviors with the introduction of suitable ligands thereinto.

TABLE 2

| | Catalyst | Conversion | Time |
|---|---|---|---|
| 14 | Example 24 | >99% | 60 min |
| 15 | Example 25 | >99% | 30 min |
| 16 | Example 26 | >99% | 20 min |

Figure 3:
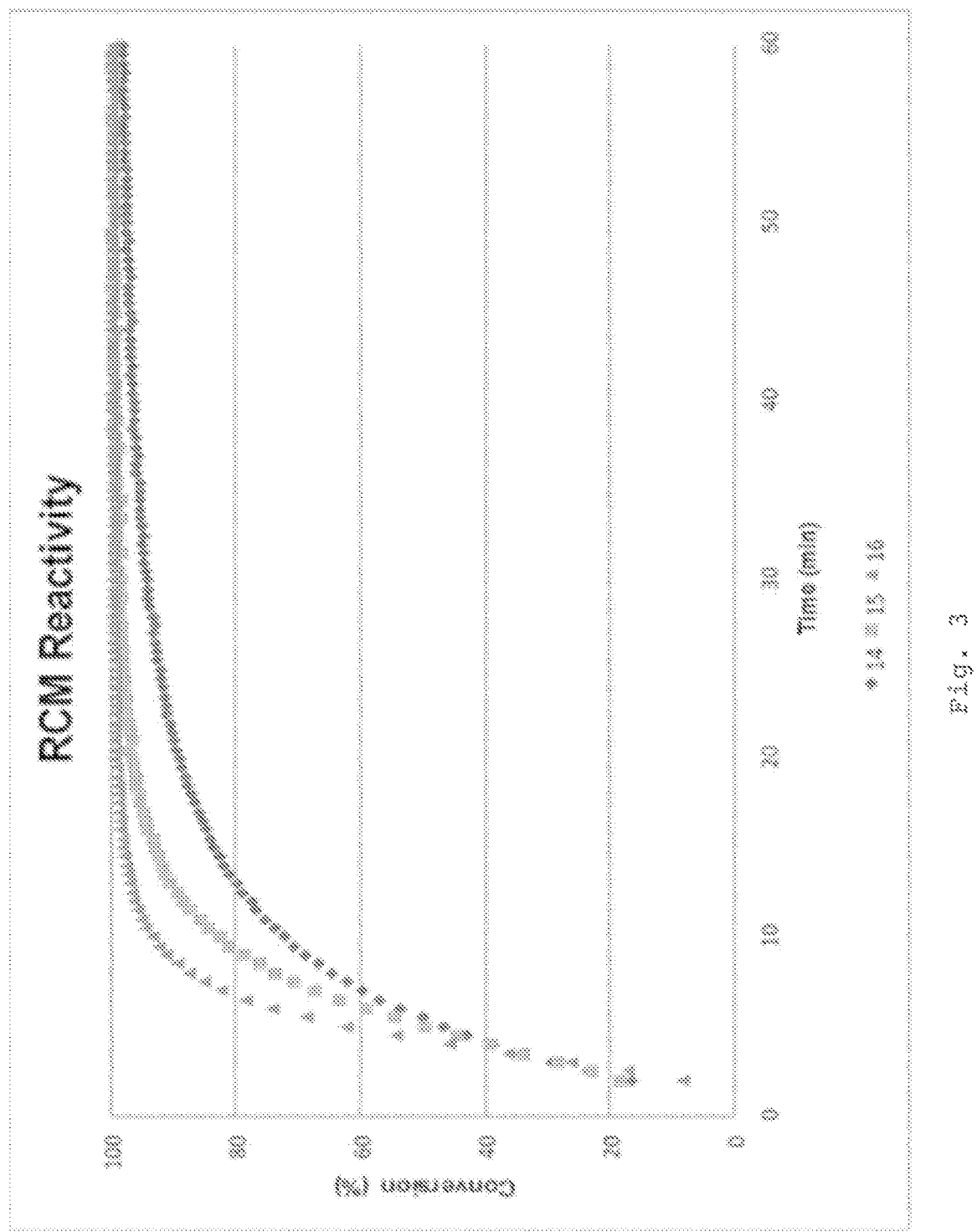
FIG. 3 depicts the activity of a catalyst containing an amide ligand prepared according to a further embodiment of the present disclosure.

In addition, as shown in Table 2 and FIG. 3, the amide ligand-containing transition metal complex according to the present disclosure exhibited a conversion rate of 99% or higher in olefin metathesis.

From the fact that the transition metal complex of Example was shorter in reaction time than those of the other Examples, it is considered that a fluorine atom in the metal complex plays a critical role in reducing the reaction time of ring-closing metathesis. In this regard, the transition metal complex of Example 13 and the following catalyst G-II were used for ring-closing metathesis and their conversion rates are given Table 3, below.

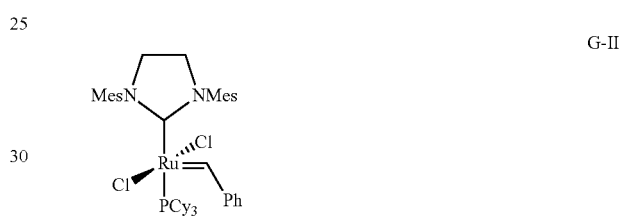

G-II

TABLE 3

| | Substrate | Product | Time (cat) | Conversion |
|---|---|---|---|---|
| 17 | EtO₂C, EtO₂C | EtO₂C, EtO₂C | 1 h (G-II) (10 min) 1 h (13) (10 min) | 98% (60%) 97% (95%) |
| 18 | HO | HO | 45 min (G-II) <1 min (13) | 60% 60% |
| 19 | p-Ts-N | p-Ts-N | 30 min (G-II) 30 min (13) | 92% 99% |
| 20 | p-Ts-N | p-Ts-N | 40 min (G-II) <1 min (13) | 90% 90% |
| 21 | Bz-N | Bz-N | 10 min (G-II) <1 min (13) | 99% 99% |

As is understood from data of Table 3, the sulfonamide ligand-containing transition metal complex of Example 13 was observed to exhibit higher conversion rates and shorter conversion time, compared to G-II.

INDUSTRIAL APPLICABILITY

The transition metal complex for olefin metathesis according to the present disclosure can be variably controlled in properties including catalytic activity, reactivity, etc., with the introduction of various substituents thereinto and thus is industrially applicable.

The invention claimed is:

1. A transition metal complex, represented by the following Chemical Formula A:

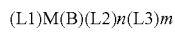

[Chemical Formula A]

wherein,

M is a transition metal of ruthenium,

L1 means a phosphine ligand or N-heterocyclic carbene ligand containing a substituted or unsubstituted alkyl of 1 to 30 carbon atoms or a substituted or unsubstituted aryl of 6 to 30 carbon atoms, L2 and L3, which are the same or different, are each a monovalent ligand selected from among a hydrogen atom, a deuterium atom, a halogen, a cyano, a substituted or unsubstituted alkyl of 1 to 30 carbon atoms, a substituted or unsubstituted aryl of 6 to 50 carbon atoms, a substituted or unsubstituted arylalkyl of 7 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted arylthioxy of 6 to 30 carbon atoms, a substituted or unsubstituted alkylthioxy of 1 to 30 carbon atoms, a substituted or unsubstituted heteroaryl of 2 to 50 carbon atoms bearing O, N, or S as a heteroatom, a substituted or unsubstituted carboxylate anion of 1 to 30 carbon atoms, and a nitrate (NO3-); or a neutral ligand selected from among a phosphine containing a substituted or unsubstituted alkyl of 1 to 30 carbon atoms or a substituted or unsubstituted aryl of 6 to 50 carbon atoms, carbon monoxide, an amine containing a substituted or unsubstituted alkyl of 1 to 30 carbon atoms or a substituted or unsubstituted aryl of 6 to 50 carbon atoms, a nitrile containing a substituted or unsubstituted alkyl of 1 to 30 carbon atoms or a substituted or unsubstituted aryl of 6 to 50 carbon atoms, and a substituted or unsubstituted aromatic heterocyclic compound of 2 to 50 carbon atoms bearing O, N, or S as a heteroatom;

in the alterative for L2 and L3, L2 and L3 are connected to each other to form a ring with M, and when L2 and L3 are each plural, the corresponding plural L2's or L3's are connected to each other to form a ring with M, n and m, which are the same or different, are each independently an integer of 0 to 2 and when n or m is 2 or greater, the corresponding plural L2's or L3's are the same or different, and A is a ligand represented by the following Structural Formula A-1 or A-2:

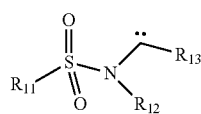

[Structural A-1]

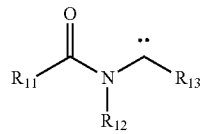

[Structural A-2]

wherein,

R11 to R13, which are the same or different, are each independently selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms bearing at least one selected from among O, N, S, and Si as a heteroatom, a substituted or unsubstituted alkoxy of 1 to 30 carbon atoms, a substituted or unsubstituted aryloxy of 6 to 30 carbon atoms, a substituted or unsubstituted alkylamine of 1 to 30 carbon atoms, a substituted or unsubstituted aryl amine of 6 to 30 carbon atoms, a substituted or unsubstituted alkylsilyl of 1 to 30 carbon atoms, a substituted or unsubstituted arylsilyl of 6 to 30 carbon atoms, a cyano, and a halogen, and '..' means a pair of electrons of carbene.

2. The transition metal complex of claim 1, wherein L2 and L3, which are the same or different, are each independently a halogen selected from among F, Cl, Br and I, and n and m are each an integer of 1 in Chemical Formula A.

3. The transition metal complex of claim 1, wherein the N-heterocyclic carbene ligand is represented by the following Chemical Formula B:

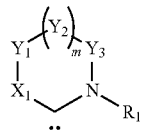

[Chemical Formula B]

wherein

X1 is selected from among O, S, N-R2, C-R3, and C-R4R5, a single or a double bond is between X1 and Y1, between Y1 and Y2, and between Y2 and Y3, Y1 to Y3, which are the same or different, are each independently selected from among N, N-R6, C-R7, and C-R8R9, m is an integer of 0 to 3, and when m is 2 or greater, the corresponding plural Y2's are the same or different, with a single or a double bond therebetween, R1 to R9, which are the same or different, are each independently selected from among a hydrogen atom, a deuterium atom, a halogen, a substituted or unsubstituted alkyl of 1 to 30 carbon atoms, a substituted or unsubstituted aryl of 6 to 50 carbon atoms, a substituted or unsubstituted arylalkyl of 7 to 50 carbon atoms, a substituted or unsubstituted cycloalkyl of 3 to 30 carbon atoms, a substituted or unsubstituted alkoxy of 1 to 30 carbon atoms, a substituted or unsubstituted aryloxy of 6 to 30 carbon atoms, and a substituted or unsubstituted heteroaryl of 2 to 50 carbon atoms bearing O, N, or S as a heteroatom, with a proviso that R1 and R2 are each neither a hydrogen atom nor a deuterium atom, and '..' means a pair of electrons in carbene.

4. The transition metal complex of claim 3, wherein the N-heterocyclic carbene ligand is one selected from among Chemical Formulas B-1 to B-13:

[Chemical Formula B-1]
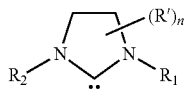

[Chemical Formula B-2]
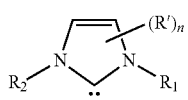

[Chemical Formula B-3]
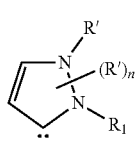

[Chemical Formula B-4]
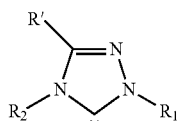

[Chemical Formula B-5]
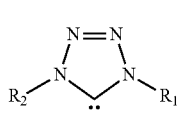

[Chemical Formula B-6]
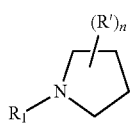

[Chemical Formula B-7]
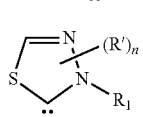

[Chemical Formula B-8]
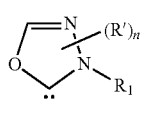

[Chemical Formula B-9]
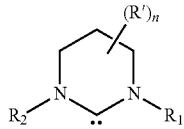

[Chemical Formula B-10]
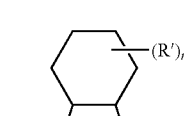

[Chemical Formula B-11]
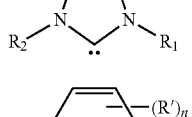

[Chemical Formula B-12]
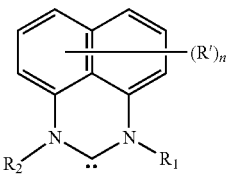

[Chemical Formula B-13]
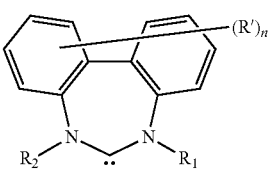

wherein R1 and R2 are each as defined above,

R' is selected from among a hydrogen atom, a deuterium atom, a halogen, a substituted or unsubstituted alkyl of 1 to 30 carbon atoms, a substituted or unsubstituted aryl of 6 to 50 carbon atoms, a substituted or unsubstituted arylalkyl of 7 to 50 carbon atoms, a substituted or unsubstituted cycloalkyl of 3 to 30 carbon atoms, a substituted or unsubstituted alkoxy of 1 to 30 carbon atoms, a substituted or unsubstituted aryloxy of 6 to 30 carbon atoms, a substituted or unsubstituted heteroaryl of 2 to 50 carbon atoms bearing O, N, or S as a heteroatom, n is an integer of 1 to 8, and when plural R's exist in one molecule, R's are the same or different.

5. The transition metal complex of claim 4, wherein the N-heterocyclic carbene is one selected from among the following Chemical Formulas B-20 to B-37:

[Chemical Formula B-20]
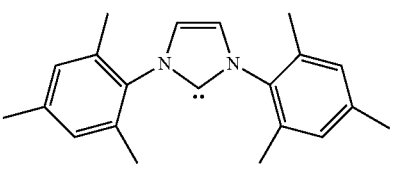

[Chemical Formula B-21]
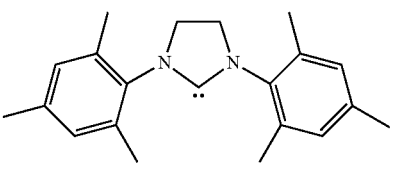

[Chemical Formula B-22]
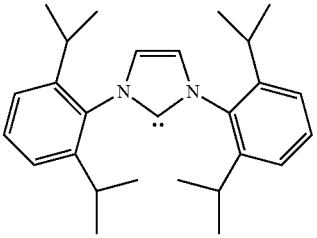

[Chemical Formula B-23]

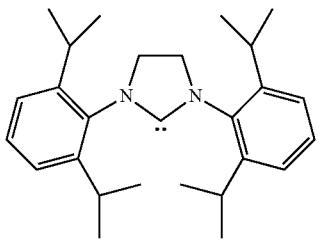

[Chemical Formula B-24]

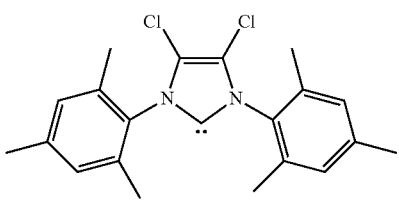

[Chemical Formula B-25]

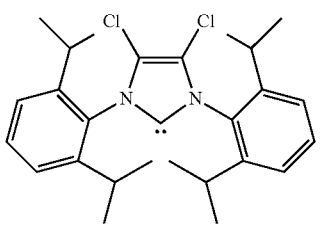

[Chemical Formula B-26]

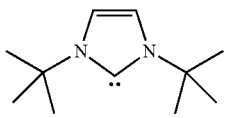

[Chemical Formula B-27]

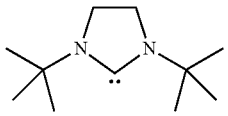

[Chemical Formula B-28]

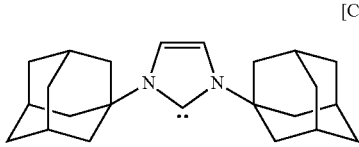

[Chemical Formula B-29]

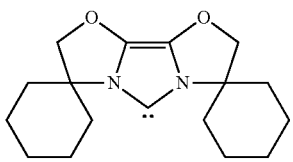

[Chemical Formula B-30]

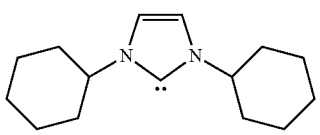

[Chemical Formula B-31]

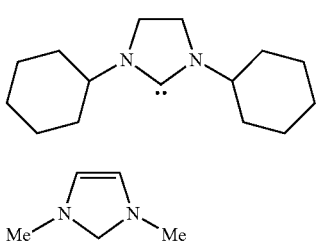

[Chemical Formula B-32]

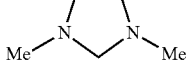

[Chemical Formula B-33]

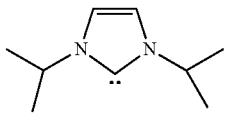

[Chemical Formula B-34]

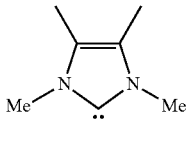

[Chemical Formula B-35]

[Chemical Formula B-36]

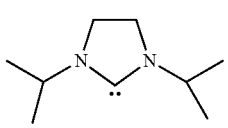

[Chemical Formula B-37]

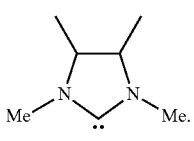

6. The transition metal complex of claim 1, wherein an oxygen atom and a carbon atom of the carbene moiety in Structural Formulas A-1 and A-2 are bound to the transition metal.

7. The transition metal complex of claim 1, wherein at least one of the substituents R11 to R13 contains a fluorine atom.

8. A method for conducting an olefin metathesis reaction, comprising using the transition metal complex of claim 1.

9. The method of claim 8, wherein the metathesis reaction is a ring-closing metathesis reaction.

10. A catalyst for olefin metathesis, prepared by supporting the transition metal complex of claim 1 on a carrier.

\* \* \* \* \*